(12) United States Patent
Lichtenstein

(10) Patent No.: US 7,513,867 B2
(45) Date of Patent: Apr. 7, 2009

(54) METHODS AND DEVICES FOR ALTERING BLOOD FLOW THROUGH THE LEFT VENTRICLE

(75) Inventor: Samuel Lichtenstein, Vancouver (CA)

(73) Assignee: Kardium, Inc. (CA)

( * ) Notice: Subject to any disclaimer, the term of this patent is extended or adjusted under 35 U.S.C. 154(b) by 859 days.

(21) Appl. No.: 10/622,129

(22) Filed: Jul. 16, 2003

(65) Prior Publication Data

US 2005/0015109 A1 Jan. 20, 2005

(51) Int. Cl.
*A61F 2/00* (2006.01)
(52) U.S. Cl. .................................................... 600/37
(58) Field of Classification Search ............ 600/37, 600/16; 606/198; 601/153; 623/904, 23.67
See application file for complete search history.

(56) References Cited

U.S. PATENT DOCUMENTS

| | | | |
|---|---|---|---|
| 4,164,046 A | 8/1979 | Cooley | |
| 5,192,314 A | 3/1993 | Daskalakis | |
| 5,961,440 A | 10/1999 | Schweich, Jr. et al. | |
| 6,024,096 A | 2/2000 | Buckberg | |
| 6,221,103 B1 | 4/2001 | Melvin | |
| 6,221,104 B1 | 4/2001 | Buckberg et al. | |
| 6,287,321 B1 * | 9/2001 | Jang | 606/200 |
| 6,332,864 B1 | 12/2001 | Schweich, Jr. et al. | |
| 6,360,749 B1 | 3/2002 | Jayaraman | |
| 6,402,680 B2 | 6/2002 | Mortier et al. | |
| 6,406,420 B1 | 6/2002 | McCarthy et al. | |
| 6,409,760 B1 | 6/2002 | Melvin | |
| 6,416,459 B1 | 7/2002 | Haindl | |
| 6,450,171 B1 | 9/2002 | Buckberg et al. | |
| 6,537,198 B1 | 3/2003 | Vidlund et al. | |
| 6,723,038 B1 | 4/2004 | Schroeder et al. | |
| 6,852,076 B2 | 2/2005 | Nikolic et al. | |
| 6,994,093 B2 | 2/2006 | Murphy et al. | |
| 7,186,210 B2 | 3/2007 | Feld et al. | |
| 7,279,007 B2 | 10/2007 | Nikolic et al. | |
| 7,303,526 B2 | 12/2007 | Sharkey et al. | |
| 2001/0044568 A1 | 11/2001 | Langberg et al. | |
| 2002/0026092 A1 | 2/2002 | Buckberg et al. | |
| 2002/0055775 A1 | 5/2002 | Carpentier et al. | |
| 2002/0161394 A1 | 10/2002 | Macoviak et al. | |

(Continued)

FOREIGN PATENT DOCUMENTS

WO  WO 90/15582  12/1990

OTHER PUBLICATIONS

Jatene, Adib, "Left Ventricular Aneurysmectomy," *J. Thorac and Card Surg*, 89:3, 1985, pp. 321-331.

(Continued)

*Primary Examiner*—Charles A. Marmor, II
*Assistant Examiner*—Christine D Hopkins
(74) *Attorney, Agent, or Firm*—Jens E. Hoekendijk

(57) ABSTRACT

An element is expanded in the left ventricle to isolate part of the left ventricle. The element has a generally convex outer surface and an apex which together define a desired geometry of the left ventricle. The isolated part of the wall of the left ventricle may be left so that the wall naturally forms around the element or the isolated portion of the ventricle may be evacuated and/or filled. The element may also be used to isolate part of the left ventricle containing a ventricular septal defect or other perforation or opening in the ventricular wall.

89 Claims, 27 Drawing Sheets

U.S. PATENT DOCUMENTS

| | | |
|---|---|---|
| 2002/0169359 A1 | 11/2002 | McCarthy et al. |
| 2002/0169360 A1* | 11/2002 | Taylor et al. .................. 600/37 |
| 2002/0188170 A1 | 12/2002 | Santamore et al. |
| 2002/0198603 A1 | 12/2002 | Buckberg et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0109770 A1 | 6/2003 | Sharkey et al. |
| 2003/0149333 A1 | 8/2003 | Alferness |
| 2003/0163191 A1 | 8/2003 | Nikolic et al. |
| 2003/0220667 A1 | 11/2003 | van der Burg et al. |
| 2004/0002626 A1 | 1/2004 | Feld et al. |
| 2004/0243170 A1 | 12/2004 | Suresh et al. |
| 2004/0249408 A1* | 12/2004 | Murphy et al. .............. 606/198 |
| 2005/0080402 A1 | 4/2005 | Santamore et al. |
| 2005/0154252 A1 | 7/2005 | Sharkey et al. |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0197716 A1 | 9/2005 | Sharkey et al. |
| 2005/0216052 A1 | 9/2005 | Mazzocchi et al. |
| 2006/0014998 A1 | 1/2006 | Sharkey et al. |
| 2006/0015002 A1 | 1/2006 | Moaddeb et al. |
| 2006/0025800 A1 | 2/2006 | Suresh |
| 2006/0030881 A1 | 2/2006 | Sharkey et al. |
| 2006/0135968 A1 | 6/2006 | Schaller |
| 2006/0135970 A1 | 6/2006 | Schaller |
| 2006/0199995 A1 | 9/2006 | Vijay |
| 2006/0229491 A1 | 10/2006 | Sharkey et al. |
| 2006/0241334 A1 | 10/2006 | Dubi et al. |
| 2006/0264980 A1 | 11/2006 | Khairkhahan et al. |
| 2006/0276683 A1 | 12/2006 | Feld et al. |
| 2006/0281965 A1 | 12/2006 | Khairkhahan et al. |
| 2007/0213578 A1* | 9/2007 | Khairkhahan et al. ......... 600/16 |

OTHER PUBLICATIONS

David et al., "Postinfarction Ventricular Septal Rupture: Repair by Endocardial Patch with Infarct Exclusion," *J Thorac and Card Surg*, 110:5, 1995, pp. 1315-1322.

Saab et al., "Left Ventricular Aneurysm: A New Surgical Approach," *Thorac Card Surg*, 37, 1989, pp. 11-19.

Menicanti, et al., "The Dor Procedure: What has Changed After Fifteen Years of Clinical Practice?," *J Thorac and Card Surg*, 124:5, Nov. 2002, pp. 886-890.

Athanasuleas et al., "Operative Techniques in Thoracic and Cardiovascular Surgery, A Comparative Altals, Surgical Anterior Centricular Restoration for Ischemic Cardiomyopathy," *An Official Publication of the Americal Association for Thoracic Surgery*, 7:2, May 2002, pp. 66-75.

Dor, Vincent, "Left Ventricular Aneurysms: The Endocentricular Circular Patch Plasty," *Seminars in Thorac and Card Surg*, 9:2, Apr. 1997, pp. 123-130.

Dor et al., "Surgery for Acquired Heart Disease, Late Hemodynamic Results After Left Ventricular Patch Repair Associated with Coronary Grafting in Patients with Postinfarction Akinetic or Dyskinetic Aneurysm of the left Ventricle," *J Thorac and Card Surg*, 110:5, 1995, pp. 1291-1301.

Cooley, Denton, "Ventricular Aneurysms and Akinesis," *Cleveland Clinic Quarterly*, 45:1, 1978, pp. 130-132.

Rivera et al., "Ventricular Aneurysms and Akinesis," *Cleveland Clinic Quarterly*, 45:1, 1978, pp. 133-135.

Torrent-Gusap et al., "Spatial Orientation of the Ventricular Muscle Band and Approach to Partial Ventriculotomy in Heart Failure," *Heart Failure: Pathogenesis and Treatment*, Ch. 36, pp. 685-693.

\* cited by examiner

METHODS AND DEVICES FOR ALTERING BLOOD FLOW THROUGH THE LEFT VENTRICLE

BACKGROUND

The present invention is directed to methods and devices for altering the function of the left ventricle. The methods and devices may be used to alter the function of the left ventricle for any reason. For example, the methods and devices of the present invention may be useful in treating congestive heart failure (CHF), ventricular aneurysms or dilation of the heart for other reasons such as coronary artery disease, hypertension, infection, or malfunctioning heart valve. The present invention may also find uses in treating ventricular septal defects or perforations of the left ventricular wall.

Various devices for altering the function of the left ventricle have been suggested. The present invention is directed to alternative devices for altering the function of the left ventricle.

SUMMARY

The present invention provides devices and methods for altering blood flow in the left ventricle and reducing pressure on an isolated or non-blood flow side. An element is provided which is movable between collapsed and expanded conditions. The element is collapsed within a delivery device and advanced into the left ventricle in the collapsed condition. The element is then expanded in the left ventricle and secured to the wall of the left ventricle to form a circumferential attachment to the wall of the left ventricle. The element separates the left ventricle into a blood flow side and a non-blood flow side with the element forming a hemostatic seal at the circumferential attachment so that pressure in the blood flow side is not communicated to the non-blood flow side. In this manner, the cyclical pressure in the left ventricle is not fully communicated, if at all, to the non-blood flow side.

The present invention is also directed to devices and methods for reducing the volume of the non-blood flow side. A reduction in volume may provide remodeling benefits when treating a dilated heart since the dilated heart often has an inefficient geometry for pumping. The volume may be reduced and maintained in a reduced volume with the element forming a hemostatic seal. The volume may be reduced by simply evacuating blood from the non-blood flow side. The volume may also be reduced by manipulating the wall of the left ventricle from within the left ventricle or using a tool which engages the outside of the heart. The volume may be reduced until a part of the wall of the left ventricle moves into contact with the element.

The element may be secured below the papillary muscles or another suitable location. For example, the element may be secured above the papillary muscles when treating a ventricular septal defect. The element may be advanced through a peripheral vessel or directly through a wall of the left ventricle. The element may be generally shaped to provide a desired geometry of the left ventricle wall. For example, the element may have an outer surface which is generally convex and has an apex.

The present invention also provides devices and methods for displacing the heart and maintaining the displaced condition with the element. The heart may be displaced by pulling, compressing or twisting the heart in a desired manner.

These and other aspects of the invention are described in the following description of the preferred embodiment, drawings and claims.

DESCRIPTION OF THE PREFERRED EMBODIMENTS

Figure 1:
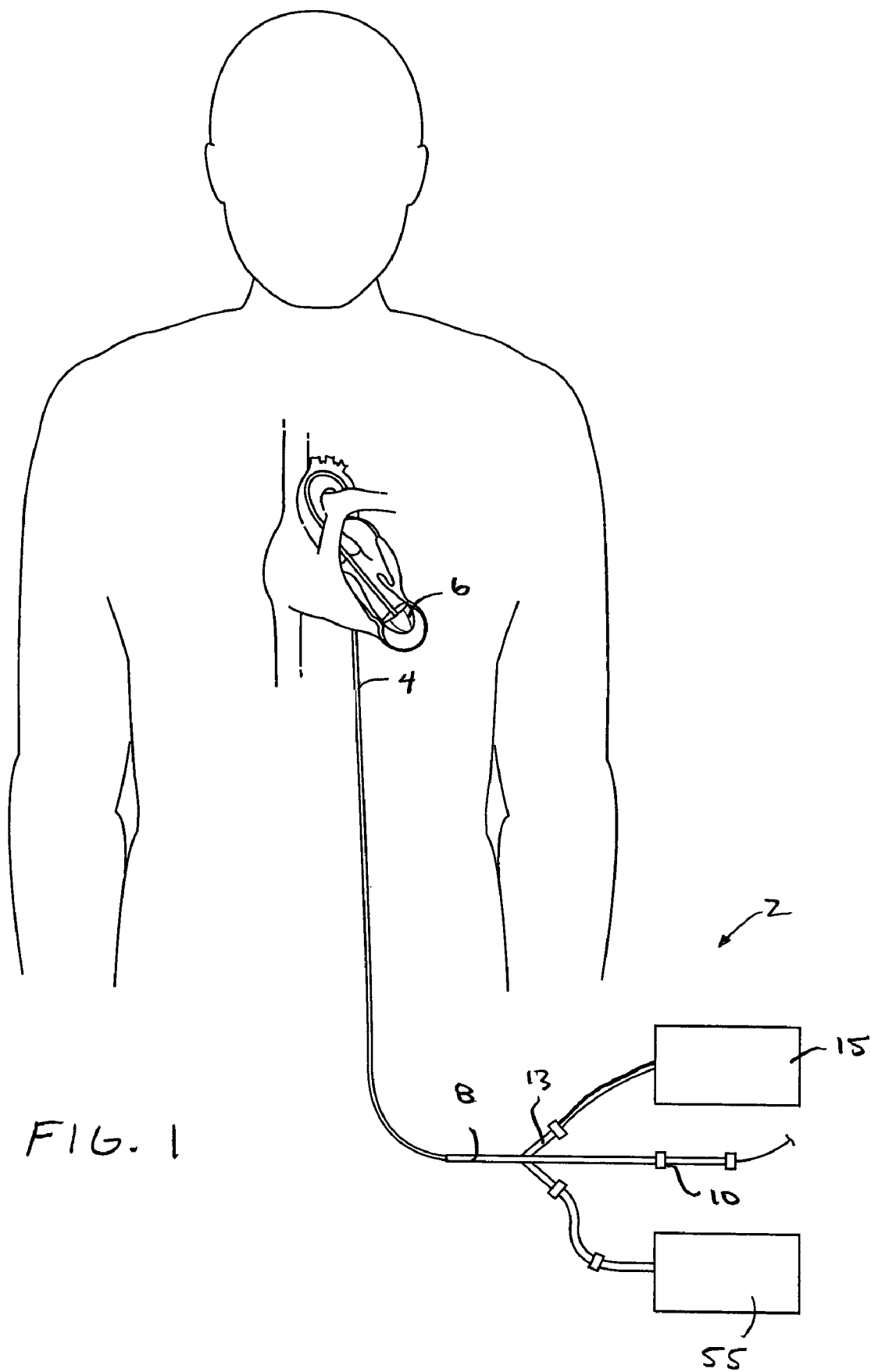
FIG. 1 shows a system which is used to alter blood flow through the left ventricle.
Figure 2:
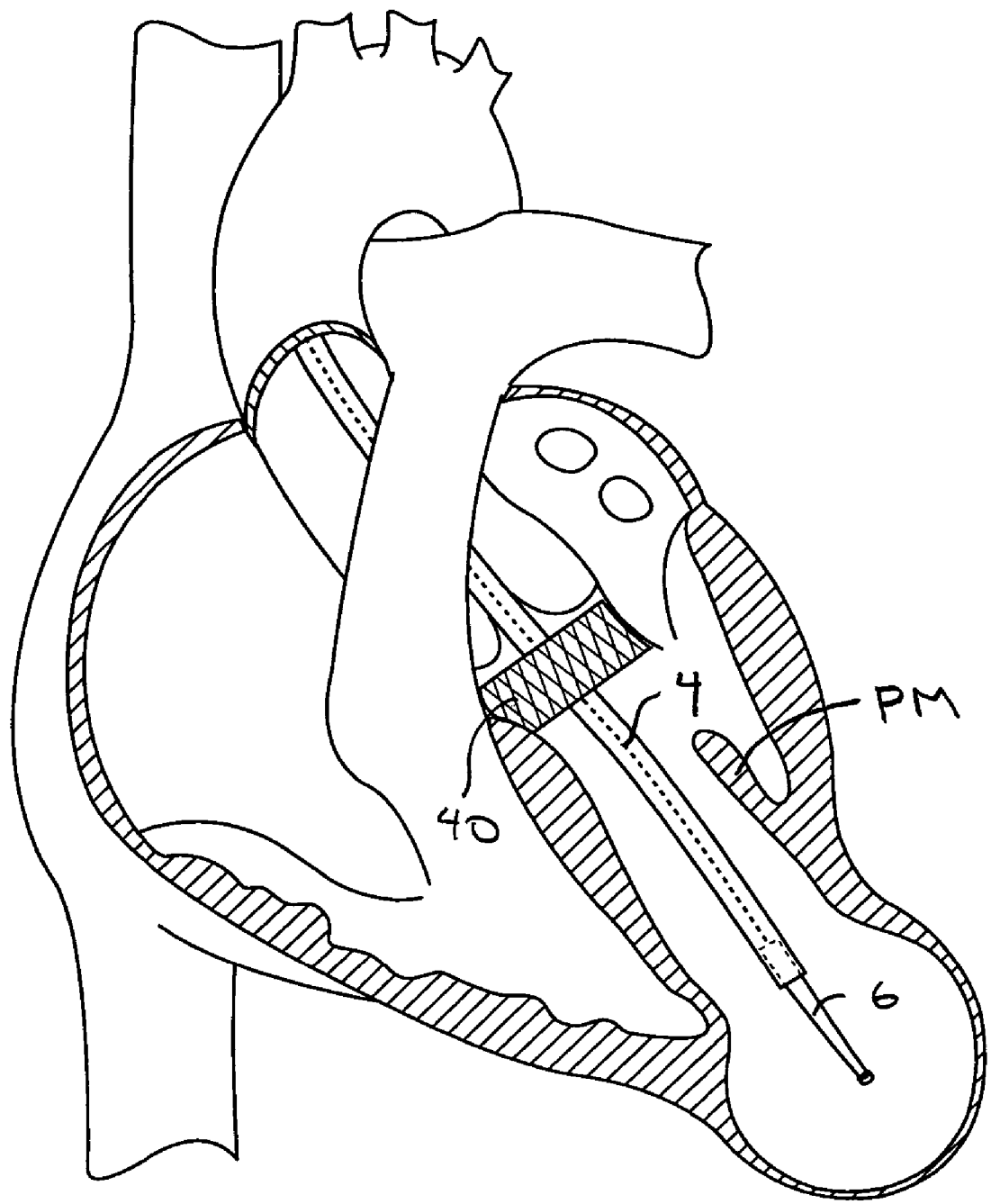
FIG. 2 shows an element contained within a delivery device.

Referring to FIGS. 1 and 2, a system 2 for altering blood flow through the left ventricle is shown. The system 2 includes a delivery device 4 for delivering an element 6 which is implanted in the left ventricle. The element 6 is collapsed within the delivery device 4 and then expanded in the left ventricle. The element 6 may be secured to the wall of the left ventricle in any suitable location as discussed below such as below the papillary muscles PM.

FIG. 1 shows the delivery device 4 introduced into the femoral artery. The delivery device 4 may, of course, be delivered through other vessels and may even be introduced directly through an opening in the left ventricle as described below. The delivery device 4 may simply be a catheter 8 which has a lumen 10 for containing the element 6. The delivery device 4 may, of course, include other features described below. Endovascular delivery of the element 6 is preferred, although not required for various aspects of the invention, since surgical procedures may have unacceptable risk for some patients.

Figure 3:
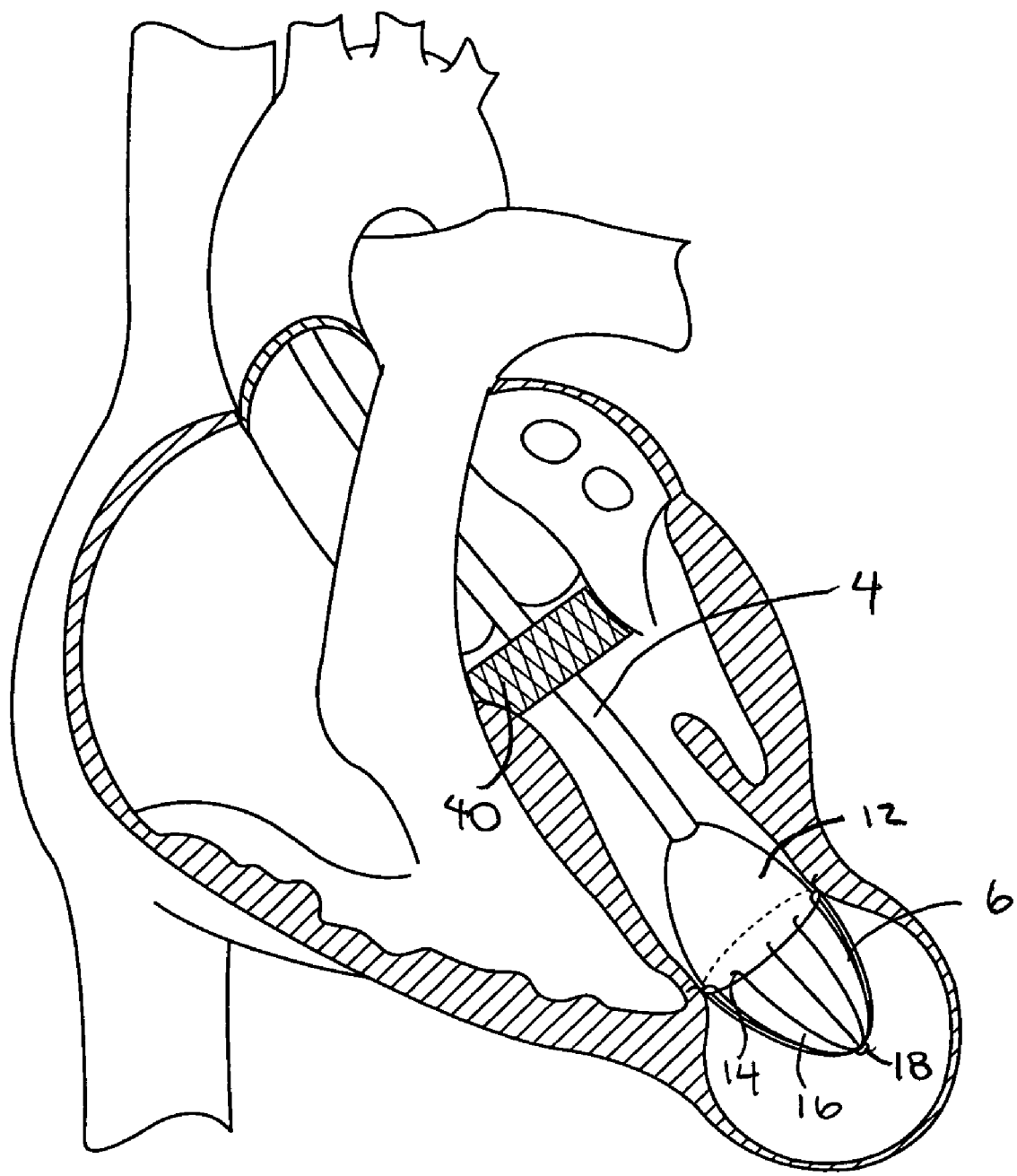
FIG. 3 shows the delivery device introduced into the left ventricle through the aortic valve with a balloon expanding the element.

The element 6 is movable between the collapsed and expanded shapes of FIGS. 2 and 3. The element 6 may be naturally biased to the expanded shape or may be expanded into the desired shape with a balloon 12 (FIG. 3), a mechanical mechanism or due to use of shape-memory materials coupled with a temperature change. The system 2 may include a balloon inflation lumen 13 and a source of inflation fluid 15, such as saline, for inflating the balloon 12 (FIG. 1). The element 6 of FIG. 3 has piercing elements 14, such as barbs, hooks harpoons, or any other suitable anchoring element to secure the element 6 to the wall of the left ventricle. The element 6 may also be secured using an energy source, such as RF, to secure the element to the wall of the left ventricle as described below. The element 6 may also be attached to the heart by evacuating blood to create a vacuum-type seal between the element 6 and the heart. As will also be discussed below, another tool may be introduced into the chest to manipulate the heart tissue and/or secure the element 6 to the left ventricle.

The element 6 has a generally convex outer surface 16 with an apex 18. The shape of the outer surface 16 is selected so that the heart will assume a more desirable shape as will be described further below. The element 6 also forms a recess 20 formed by a concave inner surface 22. The element 6 may be used to help remodel the left ventricle wall to restore the wall to a more natural shape. To this end, the element 6 may have a generally conical shape or a generally elliptical shape similar to the area around the apex of the heart (see FIGS. 4 and 5).

The element 6 has a cover 24 with a number of support members 26 secured to the cover 24. The support members 26 extend generally toward the apex 18. The support members 26 may be coupled to one another at or near the apex 18 or to a central member 29 near the apex 18. The support members 26 are attached to a circumferential band 28, which may be elastic, extending around the proximal end. The support members 26 may, for example, exert a radial force equal in sum to the left ventricular end diastolic filling pressure to secure element 6 to the left ventricular wall circumferentially and hemostatically. The support members 26 may be oriented in a manner which permits distortion particularly in a manner favoring contraction of the left ventricle. For example, the support members 26 may be somewhat flexible to permit the heart to contract. The support members 26 may be formed of any suitable material such as a stainless steel, a plastic polymer, or a superelastic material such as nitinol. The cover 24 may be any suitable biologic or biocompatible material such as mammalian (bovine or porcine) fixed pericardium, Gortex or Dacron. In particular, it may be desirable to quickly induce tissue ingrowth along the edges of the element to help seal and separate the left ventricle at the circumferential band 28. Of course, the element 6 may be formed in any other suitable manner.

Figure 12:
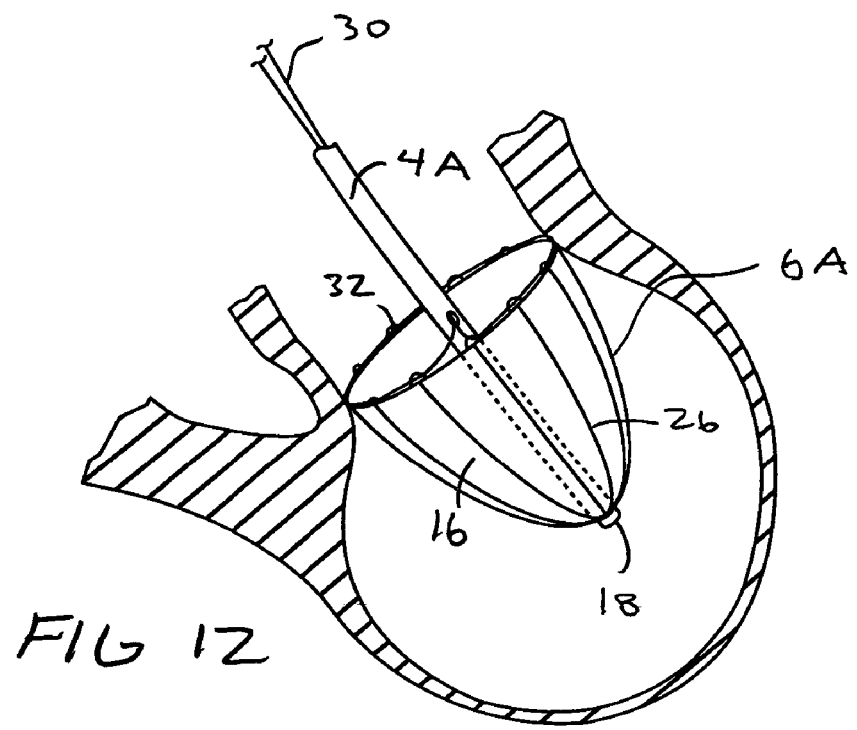
FIG. 12 shows a retractable element.
Figure 13:
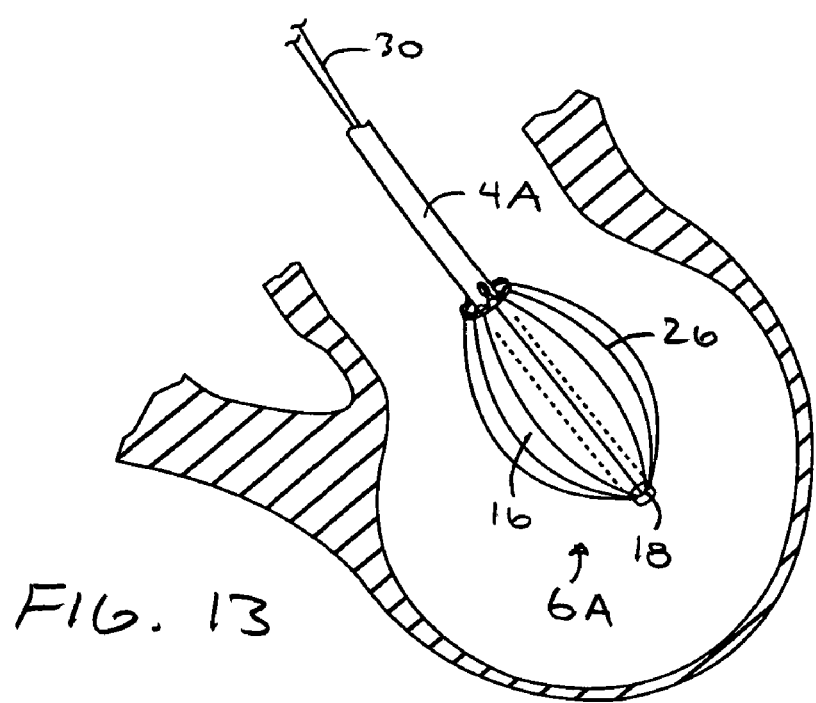
FIG. 13 shows the element of FIG. 12 retracted after expansion.

Referring to FIGS. 12 and 13, another element 6A is shown wherein the same or similar reference numbers refer to the same or similar structure. The element 6A may be retracted after expansion so that repositioning of the element 6A is possible if initial placement is not satisfactory. For example, referring to FIG. 12, a tether 30 or the like extends through loops 32 in the element 6A. The tether 30 is tensioned to cinch the tether 30 in the loops 32 thereby retracting the element 6A as shown in FIG. 13.

Figure 4:
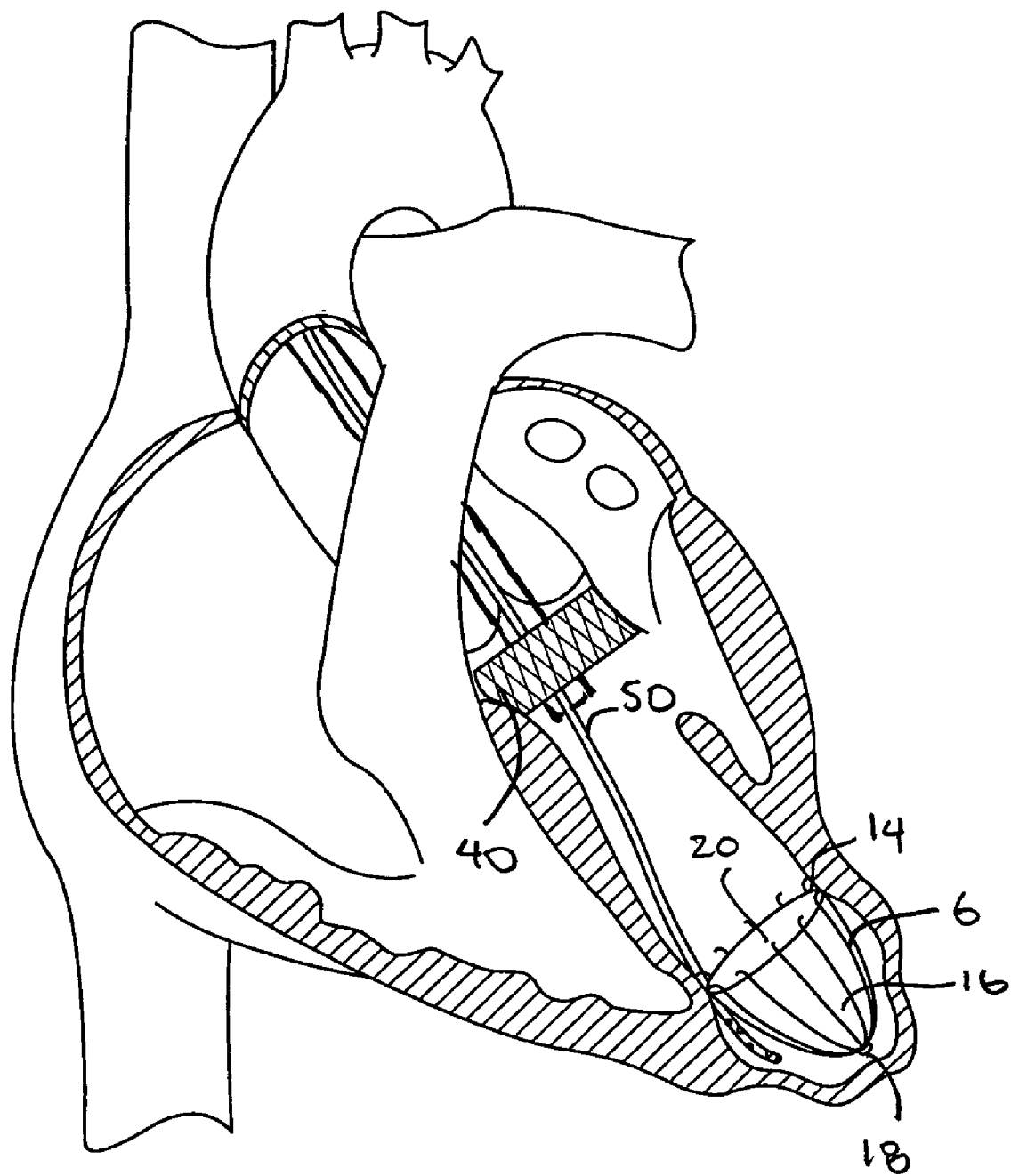
FIG. 4 shows a catheter positioned to collapse the non-blood flow side of the left ventricle.
Figure 5:
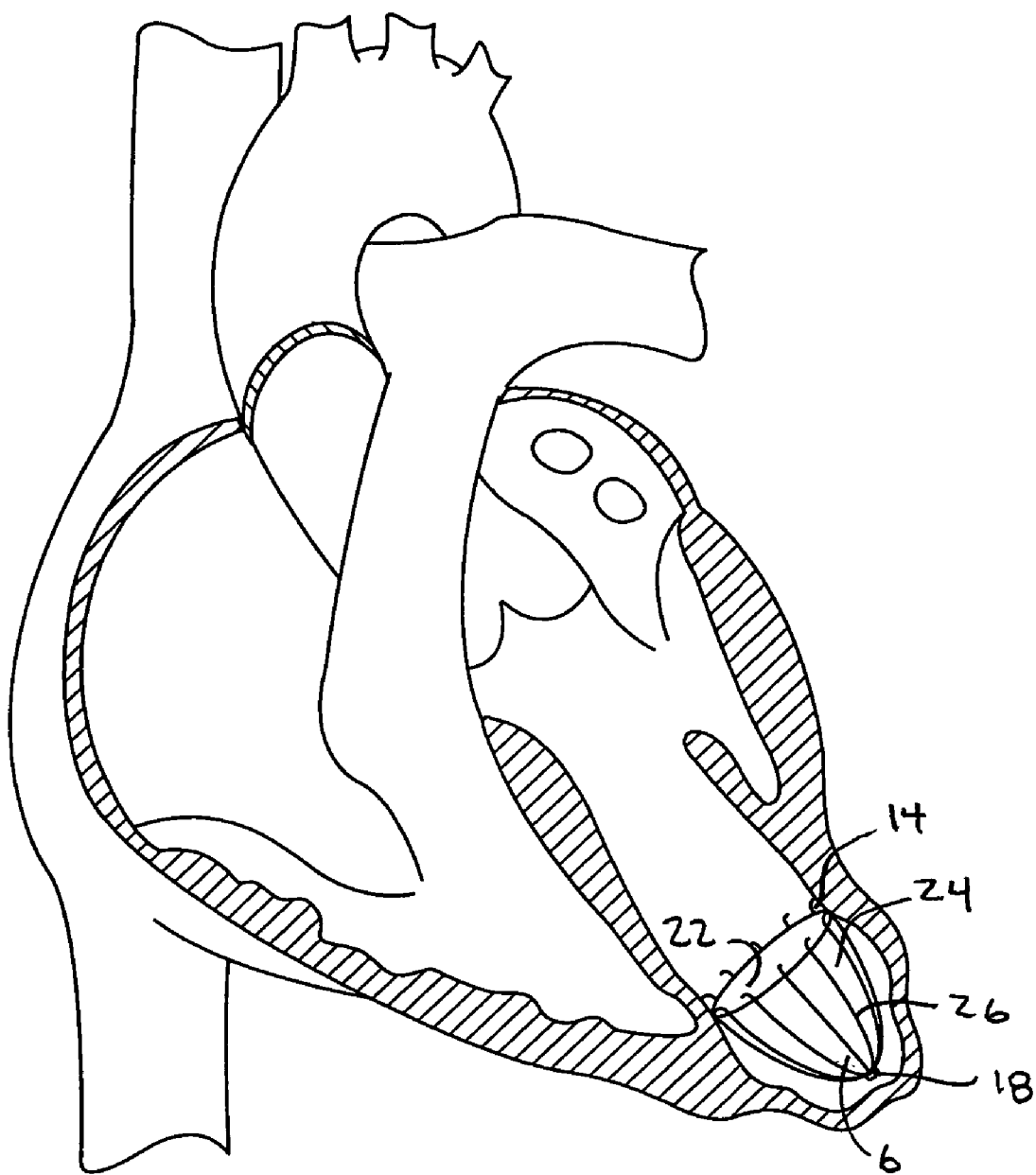
FIG. 5 shows the non-blood flow side collapsed further.
Figure 14:
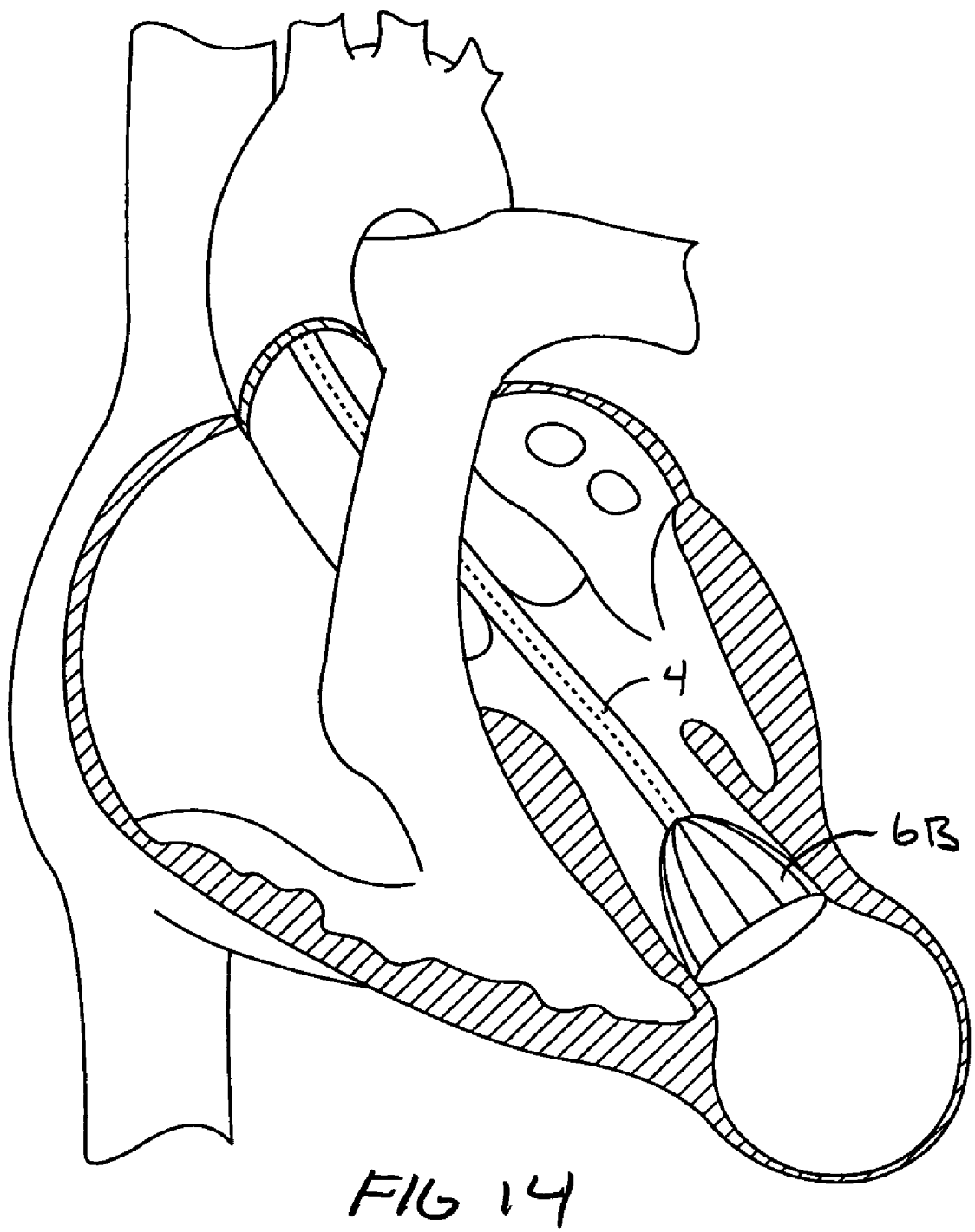
FIG. 14 shows an element which everts within the left ventricle.
Figure 15:
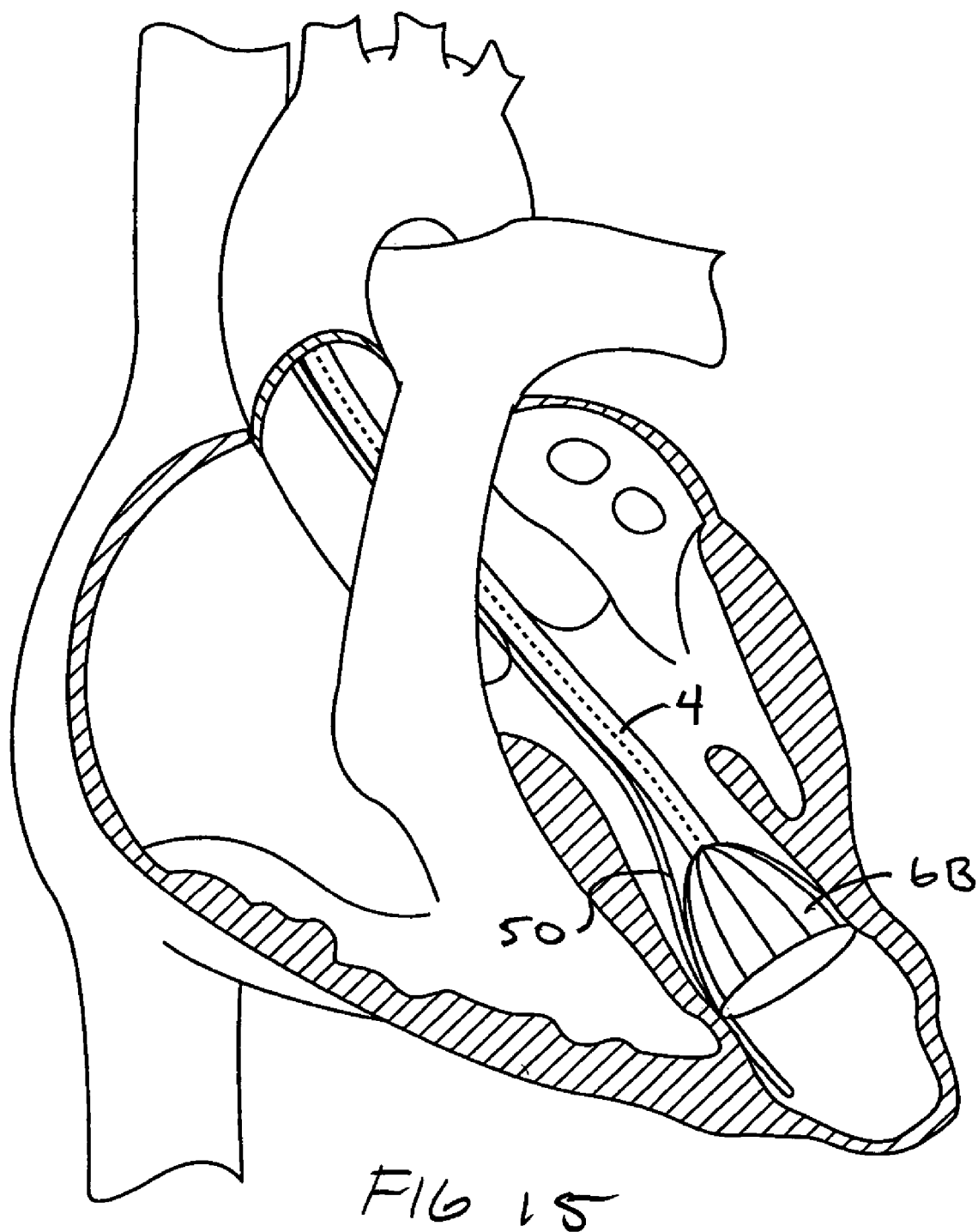
FIG. 15 shows a catheter used to evacuate the non-blood flow side prior to everting the element of FIG. 14.
Figure 16:
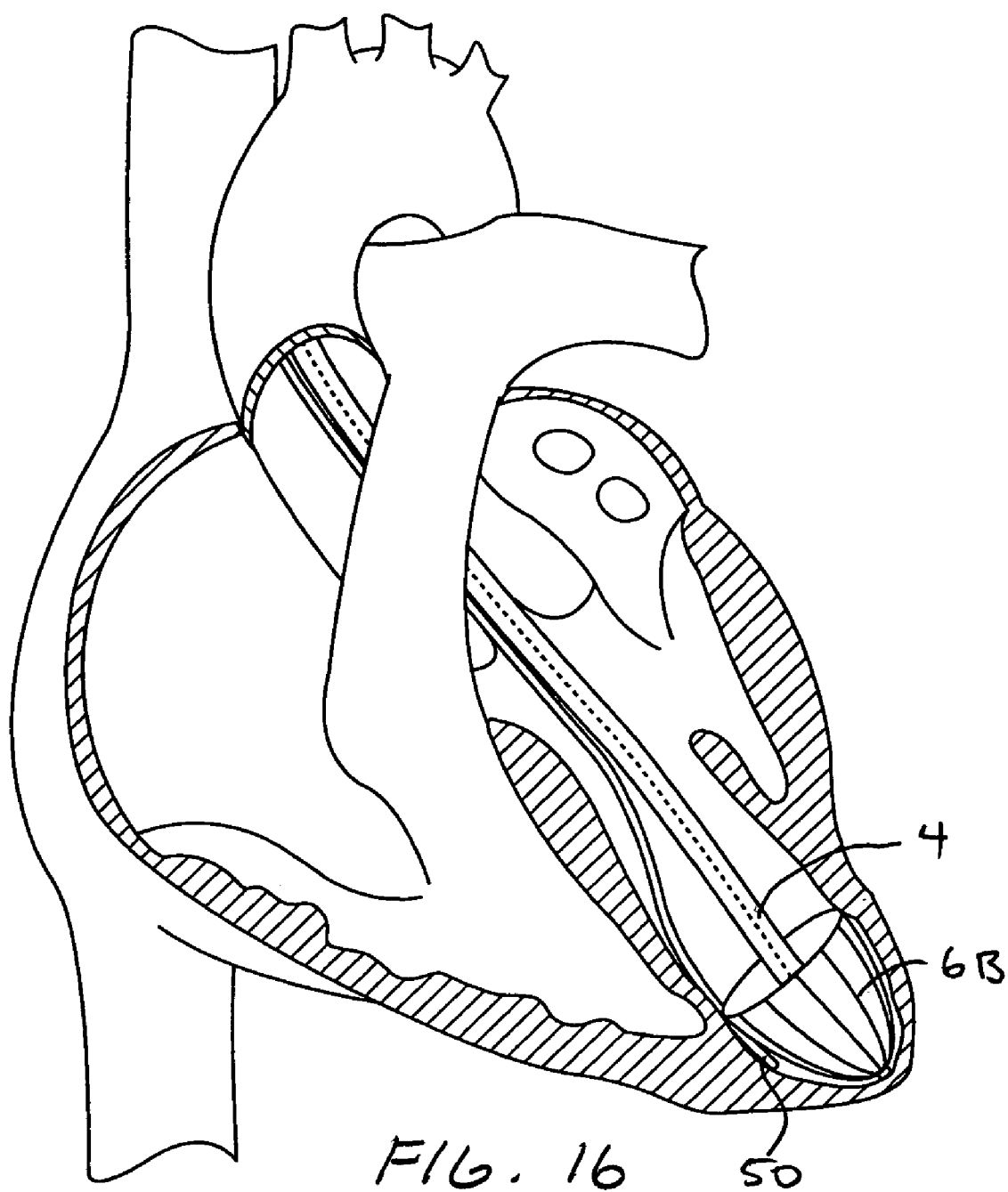
FIG. 16 shows the element of FIG. 14 everted.

Referring to FIGS. 14-16, another element 6B is shown which is everted when deployed. The element 6B is initially expanded as shown in FIG. 14. The element 6B may be expanded into engagement with the wall of the left ventricle using piercing elements such as curved barbs, hooks or needles similar to the piercing elements 14 of element 6 (FIGS. 2-4). If the position of the element 6B is not satisfactory, the element 6B may be collapsed by simply advancing the delivery device 4 over the element 6B to collapse the element 6B. The element 6B can then be repositioned and expanded again. Once the element 6B has been expanded into the desired position, the element 6B is everted as shown in FIG. 16. The piercing elements may be somewhat curved so that when the element 6A is everted the piercing elements penetrate further into the tissue. The element 6B may provide advantages in preventing thrombus or other emboli, which may be adhered to the wall of the left ventricle near the apex in akinetic or dyskinetic areas, from being dislodged and migrating past the element 6B since the element 6B is already expanded prior to being permanently anchored. As will be described below, blood in the isolated area of the left ventricle may be evacuated prior to everting the element 6B.

Referring again to FIGS. 2-4, the system 2 may also include a filter 40 which prevents thrombus or other emboli dislodged from within the left ventricle from escaping. The filter 40 may be positioned in the left ventricle which may help stabilize the system 2 in the left ventricle when deploying the element 6. The filter 40 is preferably expanded as shown in FIG. 4 prior to expanding and securing the element 6 to the wall of the left ventricle. It may be desirable to expand the filter 40 before deploying the element 6, 6A or manipulating the heart so that any thrombus dislodged during deployment or manipulation will be caught by the filter 40. Of course, the filter 40 may also be positioned at the aortic valve or in the ascending aorta without departing from the scope of the present invention. The filter 40 may be part of the delivery device 4 or may be a separate device. FIG. 4 shows the filter 40 as part of the delivery device 4 with the element 6 being delivered through the filter 40.

Use of the system 2 is now described with reference to element 6, however, it is understood that the description concerning the use of any of the elements is equally applicable to the other elements described herein or another suitable element. Before introducing the element 6 into the left ventricle, it may be necessary to determine the appropriate size and geometry of the element 6. This can be performed before introduction of the device using various known visualization techniques. The size and geometry of the element 6 may be selected to achieve a desirable shape for the heart. For example, the element 6 may help restore a dilated heart toward a more normal geometry. Of course, the present invention may be accomplished with a number of different sizes and geometries or the element 6 itself may be flexible enough to accommodate a range of size requirements. The present invention may also be practiced with the element 6 being specifically designed with the particular geometry of the patient's heart in mind including not only the overall geometry of the heart and left ventricle but also the size and extent of non-functioning areas and the location of transition zones between functioning and non-functioning areas.

In some applications, the element 6 is secured to the wall of the left ventricle at or near the transition zone between functioning and non-functioning parts of the wall of the left ventricle. In this manner, the amount of functioning wall of the left ventricle remaining in the blood flow path is maximized. For other applications, it may be desirable to secure the element 6 just within functioning parts of the wall of the left ventricle. For example, the element 6 may be somewhat compliant or resilient so that the heart is not overly restrained during contraction. Of course, the element 6 may also simply be positioned at a more fixed location such as below the papillary muscles. For example, the element may be positioned less than one cm below the papillary muscles. This position may be within the functioning part of the wall of the left ventricle thereby excluding some portion of the wall of the left ventricle upon deployment of the element 6.

As mentioned above, the delivery device 4 may be used to deliver the element 6 endovascularly when introduced through a peripheral vessel such as the femoral artery as shown in FIG. 1. Of course, the element 6 may be delivered through other endovascular paths such as a venous route across the atrial septum into the left atrium, and then across the mitral valve into the left ventricle. The element 6 is held in the collapsed position by the delivery device 4. The delivery device 4 is passed through the aortic valve and into the left ventricle. The element 6 is then moved out of the delivery device 4 by advancing the element 6 and/or retracting the delivery device 4. The element 6 may now be expanded and secured to the wall of the left ventricle. The element 6 may naturally expand into engagement with the wall or may be balloon expanded or mechanically expanded (FIG. 3). The filter 40 (FIG. 4) may be expanded prior to expansion of the element 6 within the left ventricle to prevent any thrombus dislodged during the procedure from migrating downstream.

Figure 6:
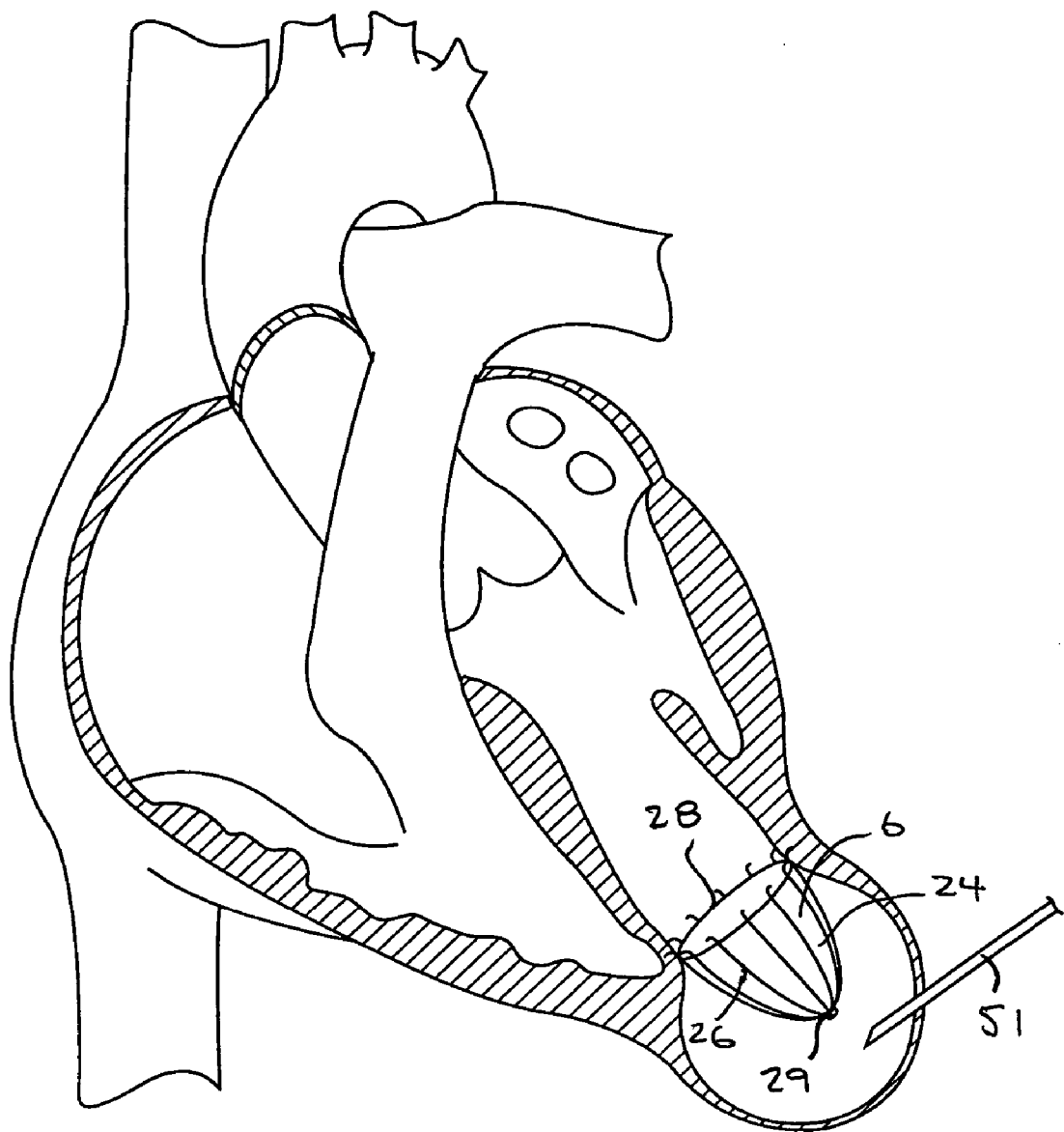
FIG. 6 shows a needle piercing the non-blood flow side to evacuate blood from the non-blood flow side.

Once the element 6 is secured to the wall of the left ventricle, the element 6 has essentially separated the left ventricle into a blood flow side and a non-blood flow side. The blood flow side continues to form part of the blood flow path through the heart while the non-blood flow side, or isolated side, does not. The blood on the non-blood flow side may be partially or completely evacuated through the delivery device 4, a separate catheter 50 which is subsequently removed (FIG. 4), or simply with a needle 51 which pierces the wall of the left ventricle (FIG. 6). Evacuation of blood may provide the benefits described below such as partial remodeling of the heart wall and reduction in further dilation of the heart.

Figure 7:
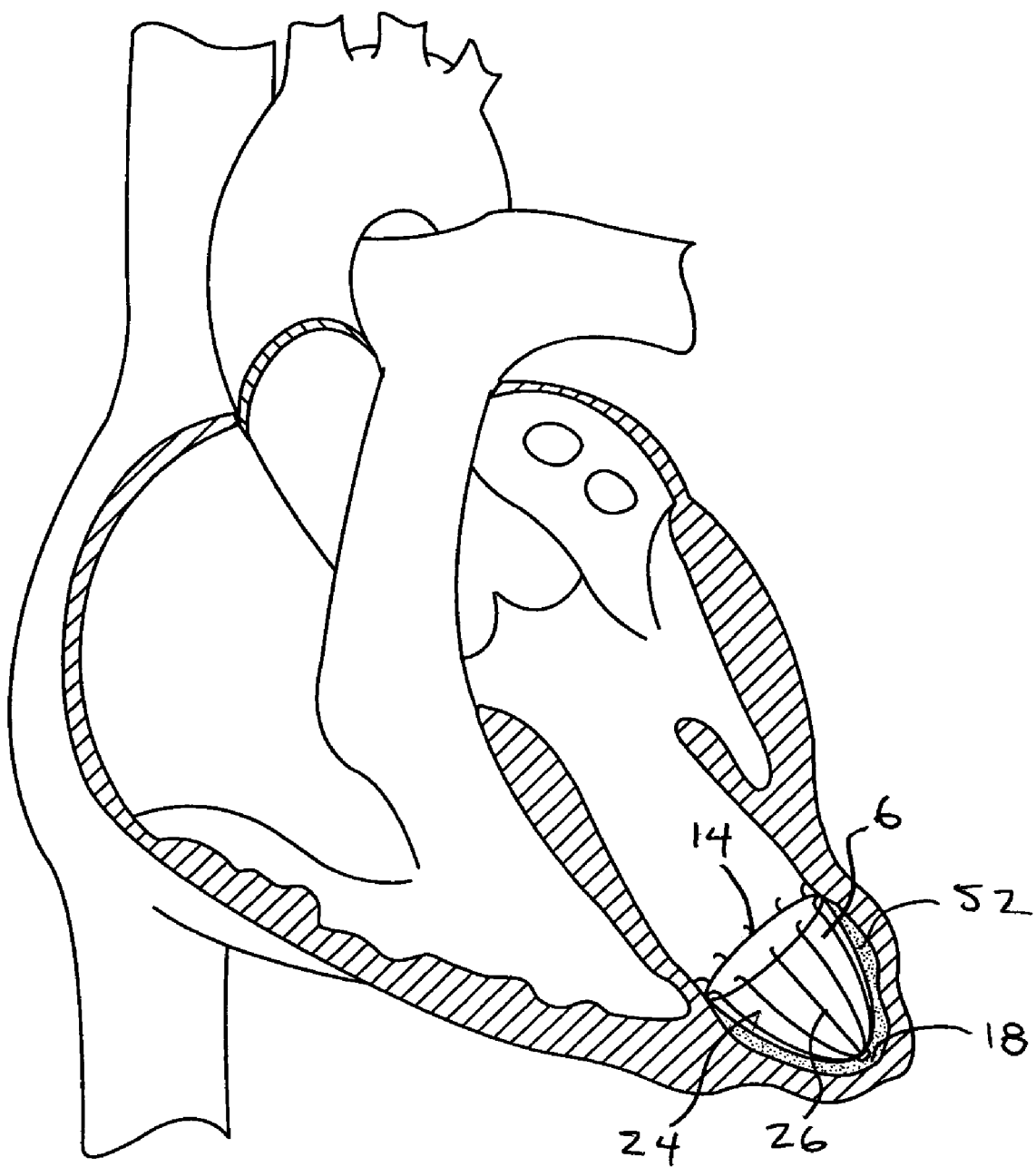
FIG. 7 shows a material introduced into the evacuated part of the left ventricle.
Figure 8:
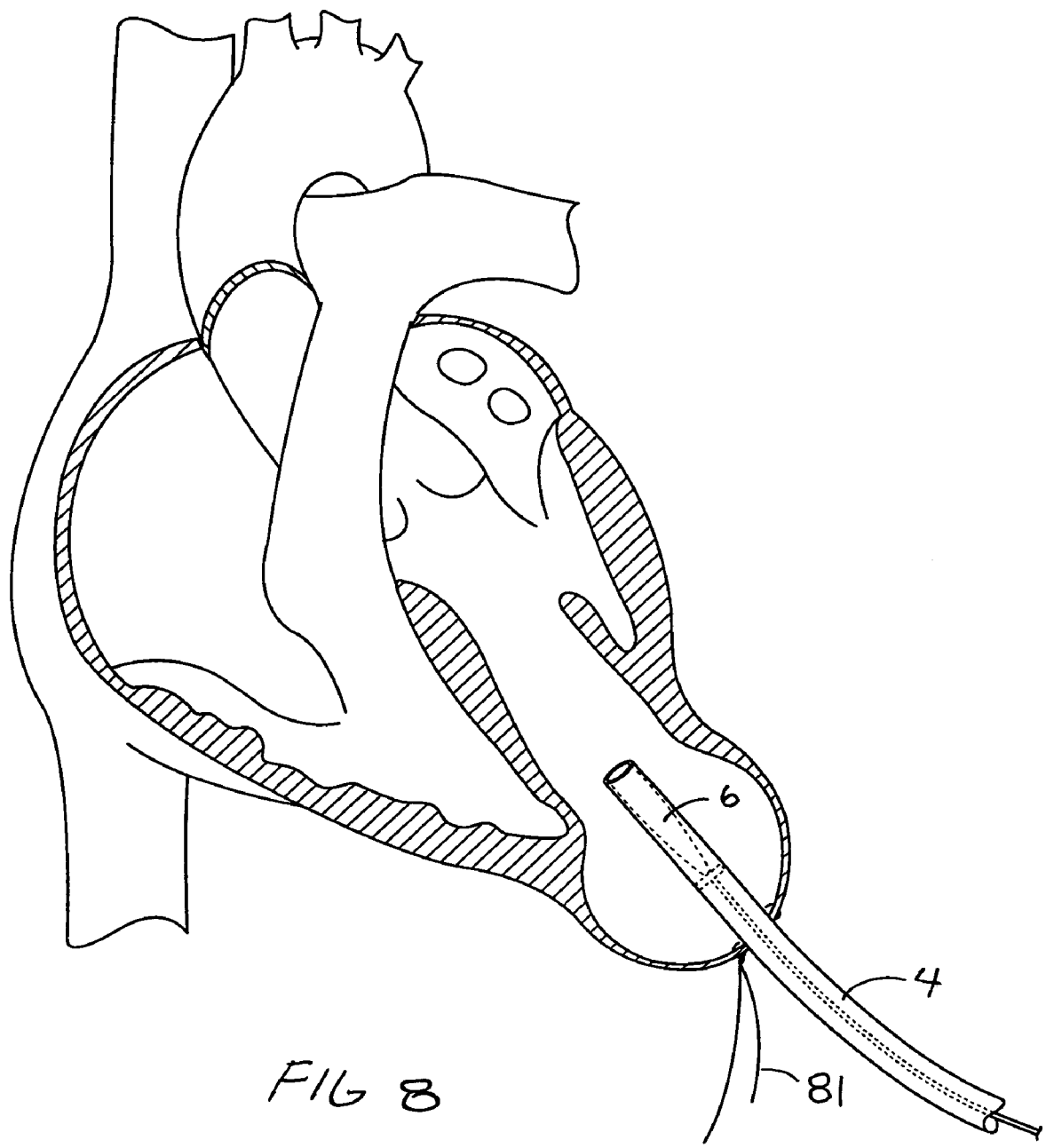
FIG. 8 shows the delivery device introduced directly through the wall of the left ventricle.
Figure 9:
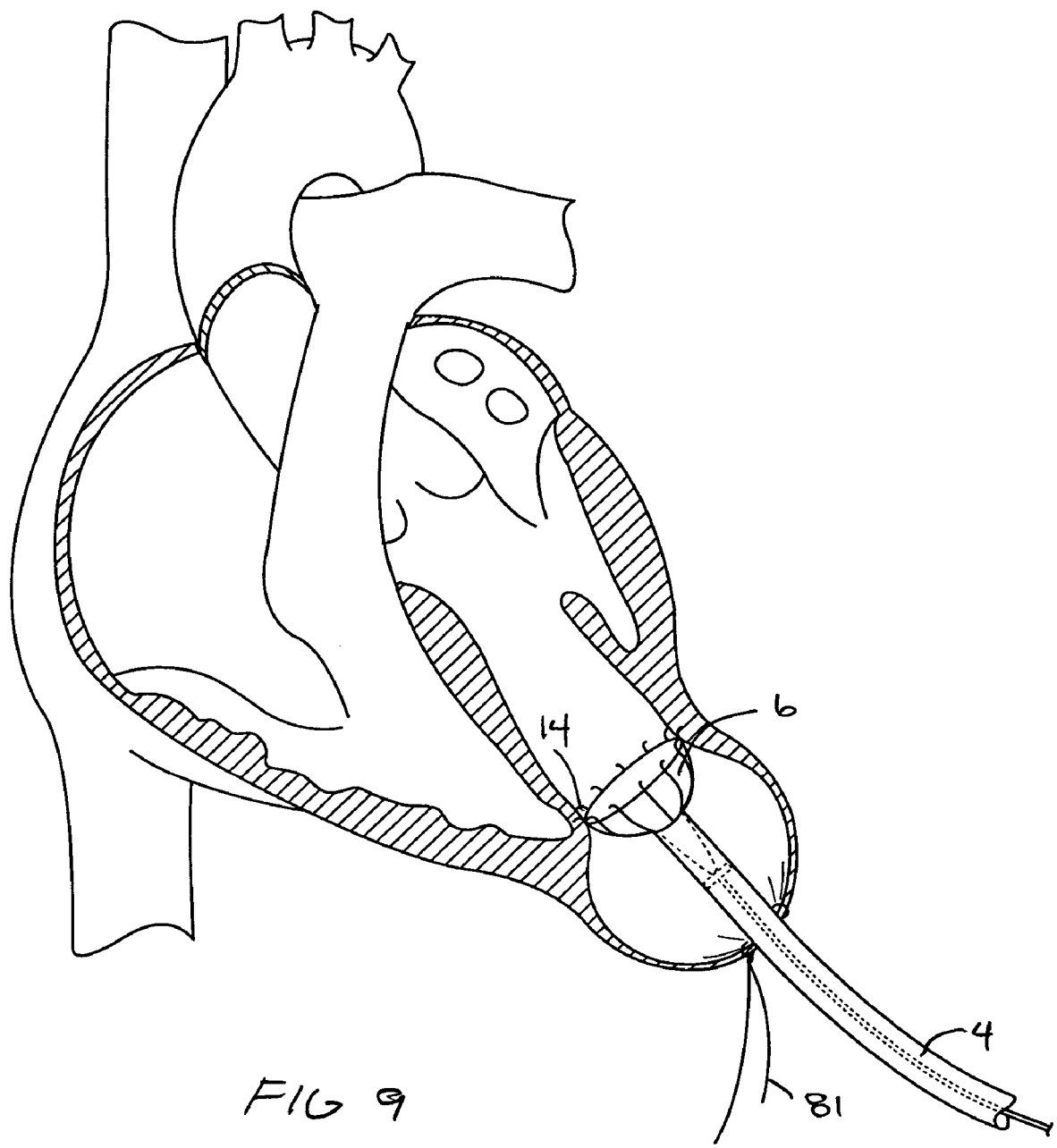
FIG. 9 shows the element partially expanded in the left ventricle.
Figure 10:
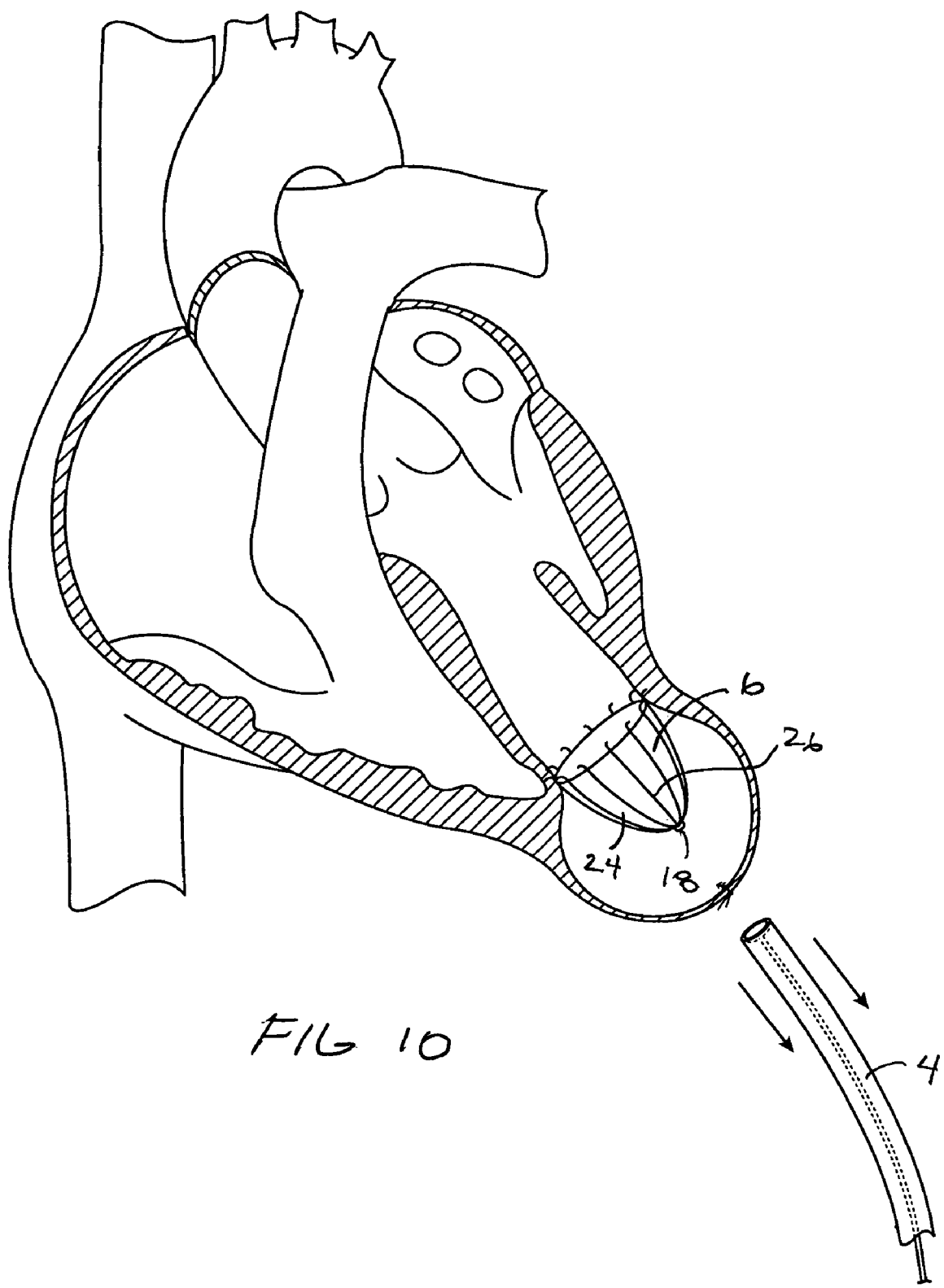
FIG. 10 shows the element fully expanded and the delivery device removed.
Figure 11:
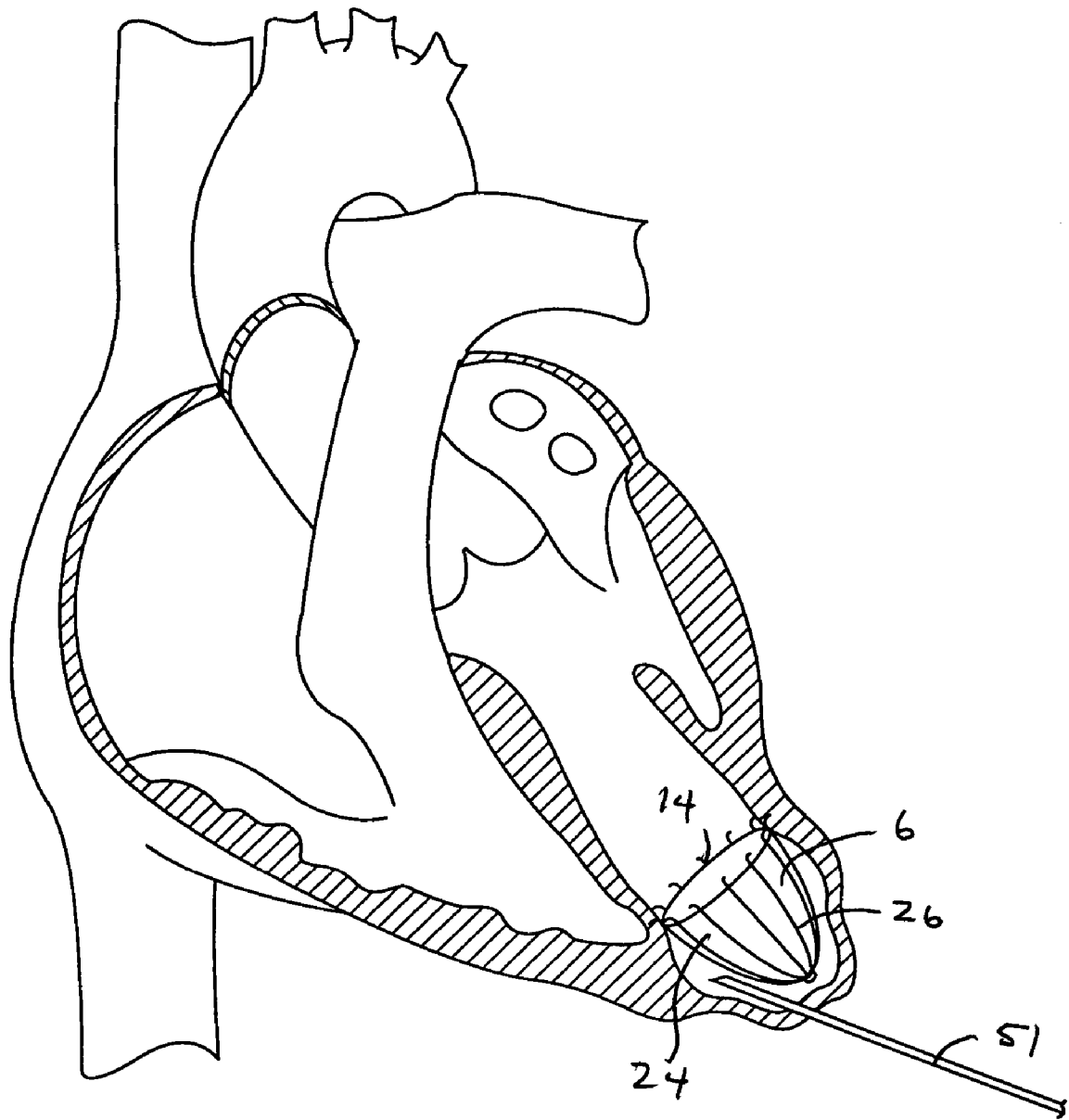
FIG. 11 shows a needle piercing the left ventricle to evacuate the non-blood flow side.

The blood may be evacuated until at least part of the wall of the left ventricle on the non-blood flow side moves into contact with the element 6 or until a low pressure threshold is reached (FIG. 7). Evacuation of blood may also create a vacuum-type seal between the heart and the element 6 which can be used to secure or help secure the element 6 to the heart. When using the element 6B of FIGS. 14-16 in particular, the isolated or non-blood flow side is partially evacuated prior to everting the element 6B as shown in FIG. 15 so that pressure does not build in the isolated side and impede the element from everting as shown in FIG. 16. After everting the element 6B, further evacuation of blood may be desirable. Of course, various aspects of the present invention may be practiced without evacuating blood from the isolated side.

The isolated side may also be injected with a material 52 after removing some or all of the blood as shown in FIG. 7 to fill any space which may exist between the element and the isolated part of the heart. The material 52 may be used to induce thrombus formation in any remaining space in the isolated region and may render the element 6 hemostatic. Alternatively, the material 52 may have adhesive qualities which help hold the wall of the left ventricle in the collapsed shape after evacuating the blood. As shown in FIG. 7, the distended portion of the wall is somewhat wrinkled after evacuating blood from the isolated region. The material 52 may help prevent the wrinkled portion from re-expanding. Of course, the isolated region may not re-expand simply due to the fact that the element 6 forms a seal with the wall of the left ventricle thereby preventing blood from entering the isolated region to re-expand or re-inflate the isolated region. The material 52 may be delivered through the device 4 from a source of the material 55 (see FIG. 1) or through the catheter 50 or needle 51.

Figure 17:
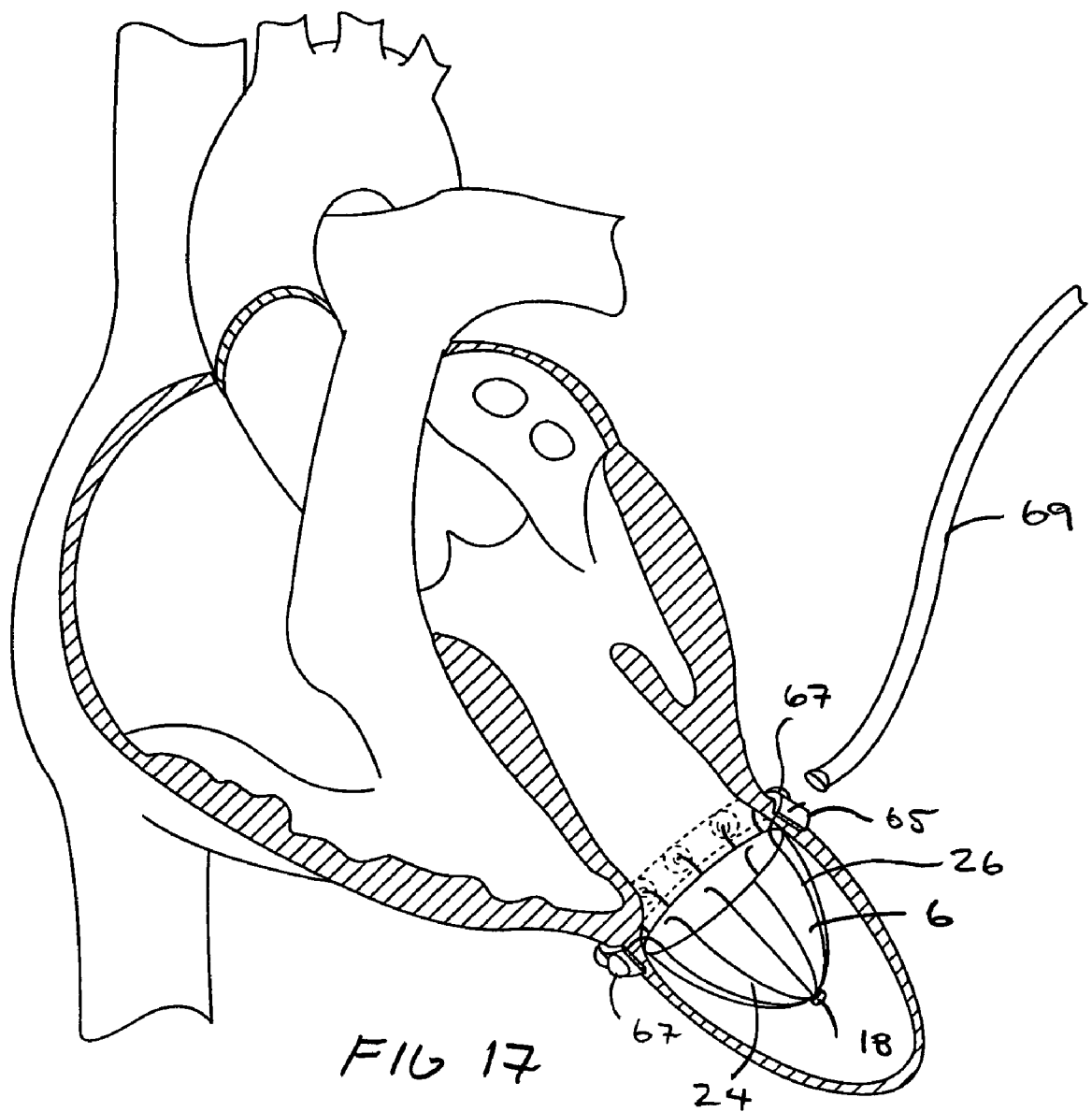
FIG. 17 shows an external member which engages the element and a tool used to secure the element to the wall of the left ventricle.
Figure 18:
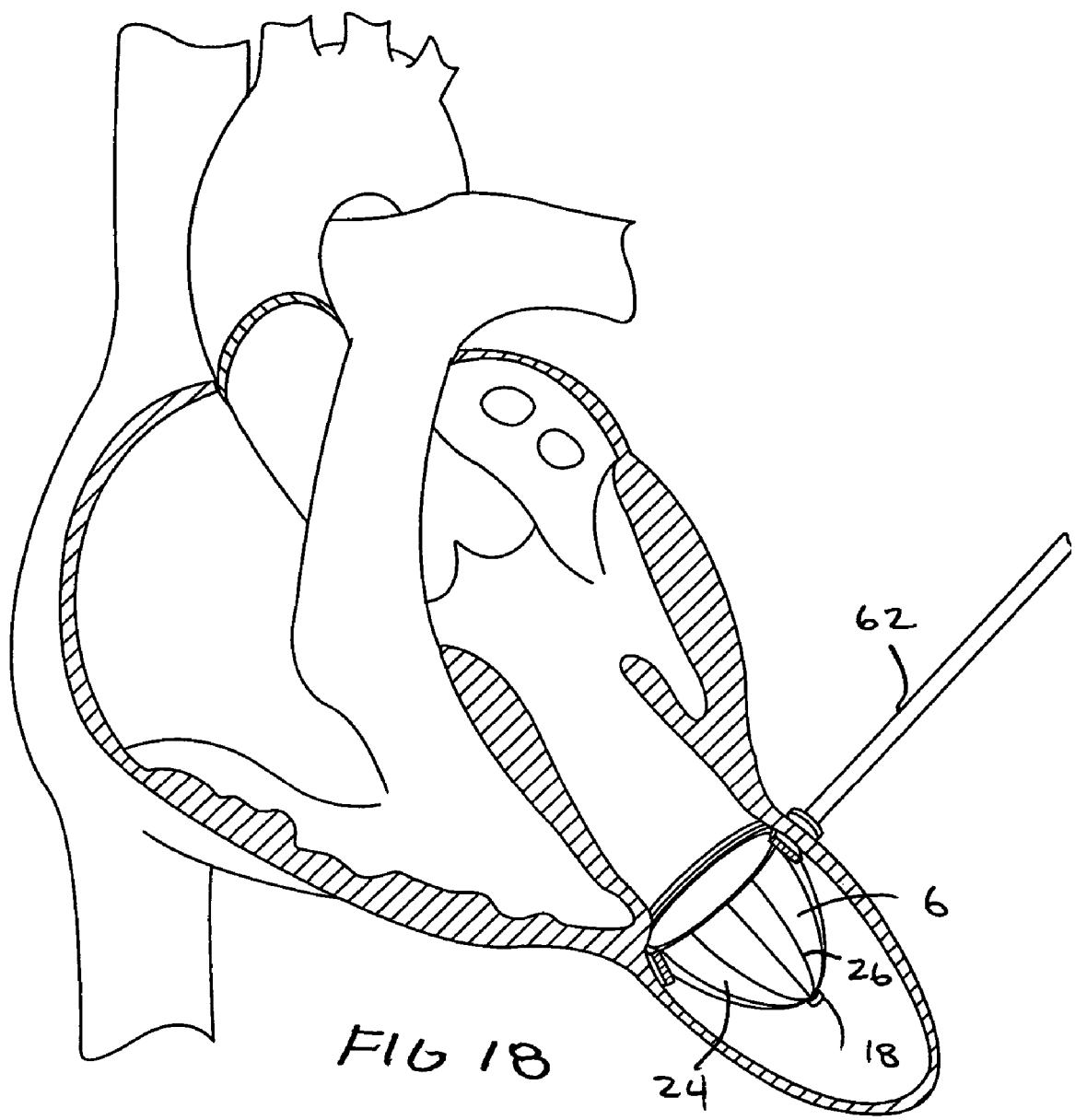
FIG. 18 shows the tool being used to deliver RF energy to secure the element to the wall of the left ventricle.

Referring to FIG. 17, an external member 65 may also be provided which traps the wall of the left ventricle. The external member 65 may be a band which locks to the element 6 by itself or a number of parts 67 which engage the element 6 and are delivered by a tool 69 from outside the heart. For example, each part 67 may lock to one of the piercing elements 14 as shown in FIG. 18 with or without use of the external member 65 or band. Referring to FIG. 18, an attachment tool 62 may also be used to help form a circumferential seal between the element 6 and the wall of the left ventricle. The attachment tool 62 may deliver energy, such as RF energy, to secure the element 6 to the left ventricle wall. The delivery device 4 or element 6 itself may also include another electrode (not shown) for use of bipolar RF.

Figure 19:
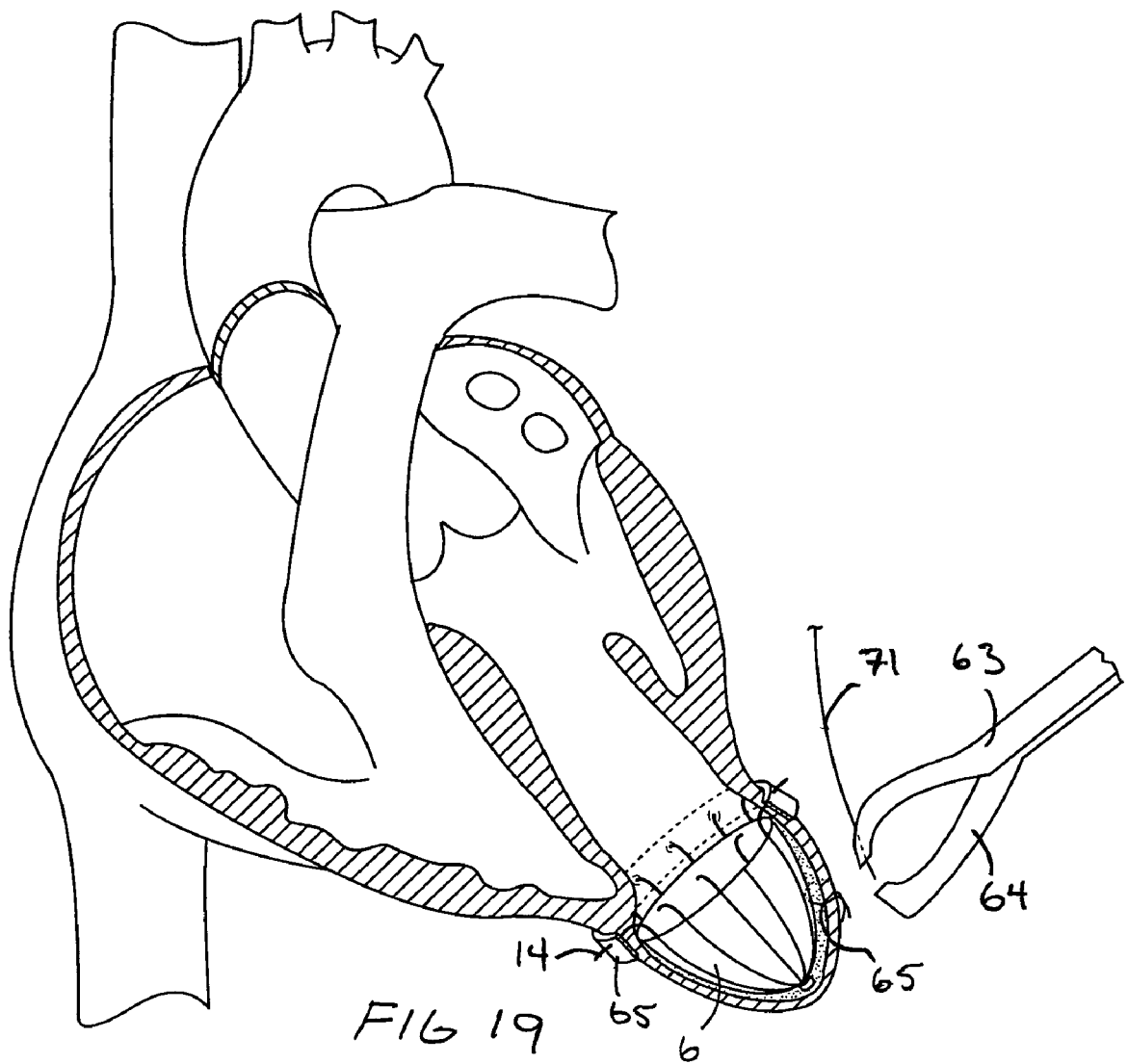
FIG. 19 shows another tool used to secure the element to the wall of the left ventricle.
Figure 20:
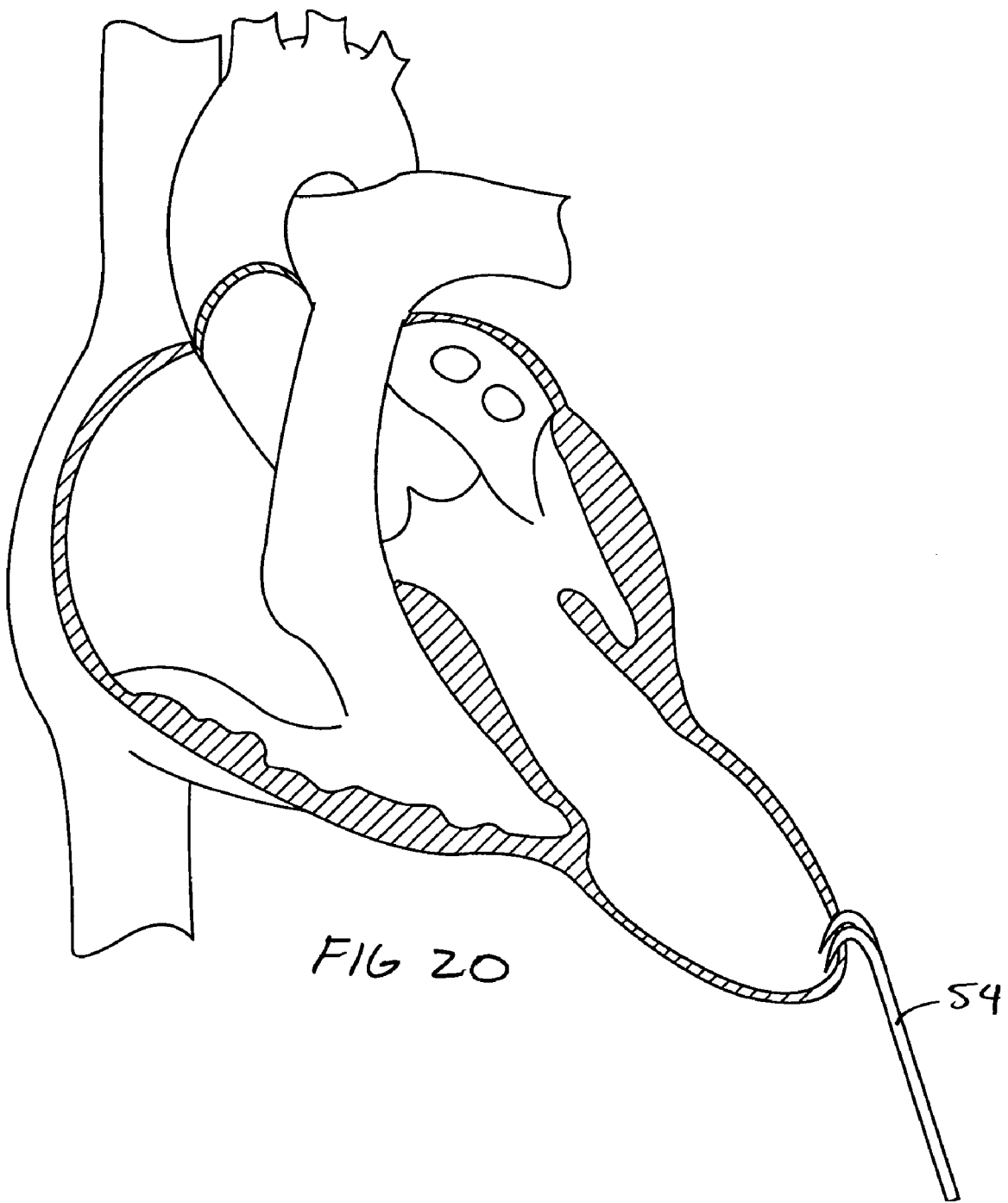
FIG. 20 shows the heart displaced prior to deploying the element.

Referring to FIG. 19, another attachment tool 63 is shown which is used to attach the element 6 to other parts of the left ventricle. The tool 63 drives an attachment element 65 through the left ventricle wall and into engagement with the element 6. For example, the tool 63 may be a suturing device 64 which delivers a suture 71 to attach the element 6 to the heart. Securing the element 6 to the wall of the left ventricle at locations other than the circumferential region may help provide a fluid tight seal around the element 6. Securing the element 6 to the left ventricle may also be used to retain desired displacements and loads or to achieve a desired shape as described further below. The tool 63 and element 6 may be configured so that the tool 63 may be used to attach the element 6, such as parts of the cover 24, to the heart at locations selected by the user.

Figure 21:
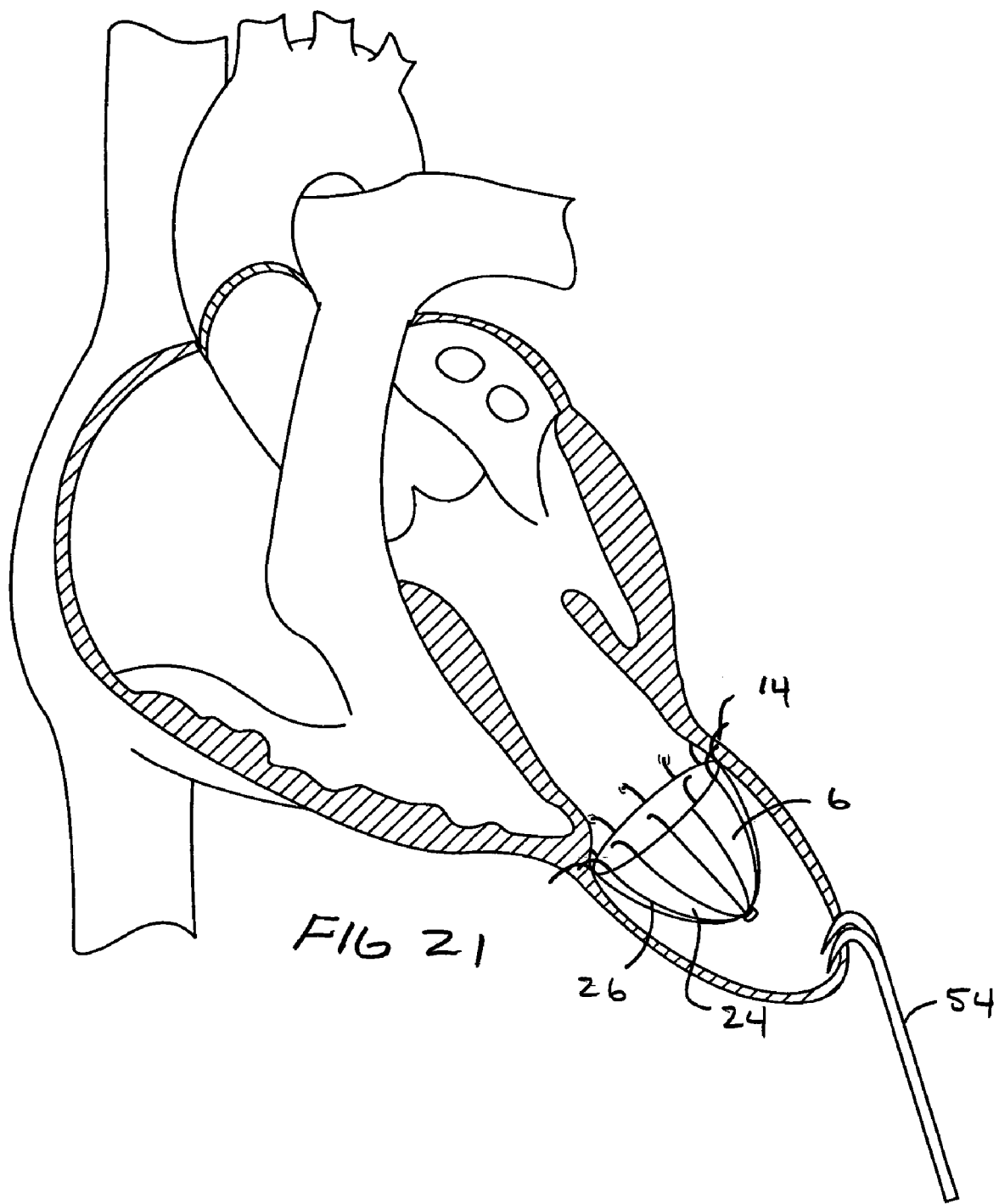
FIG. 21 shows the element deployed after displacing the heart.

Referring to FIGS. 20-27, the system 2 may also be used in combination with a tool 54 which manipulates the heart and/or helps to secure the element 6 to the left ventricle. The tool 54 may be used to change the shape of the heart or to move or displace the heart into engagement with the element 6 as necessary. For example, it may be desirable to alter the geometry of the left ventricle prior to attachment of the element 6. The altered geometry may help to restore a more advantageous geometry for pumping or it may be used to place the left ventricle under compression, tension or torsion. For example, it may be desirable to compress or tension the heart prior to attaching the element 6 so that the left ventricle wall is under compression when secured to the element 6 as shown in FIG. 21. Once the heart is tensioned or compressed as desired, the element 6 can be deployed. The element 6 may help to retain part or all of the desired displacement or loading on the heart.

Figure 22:
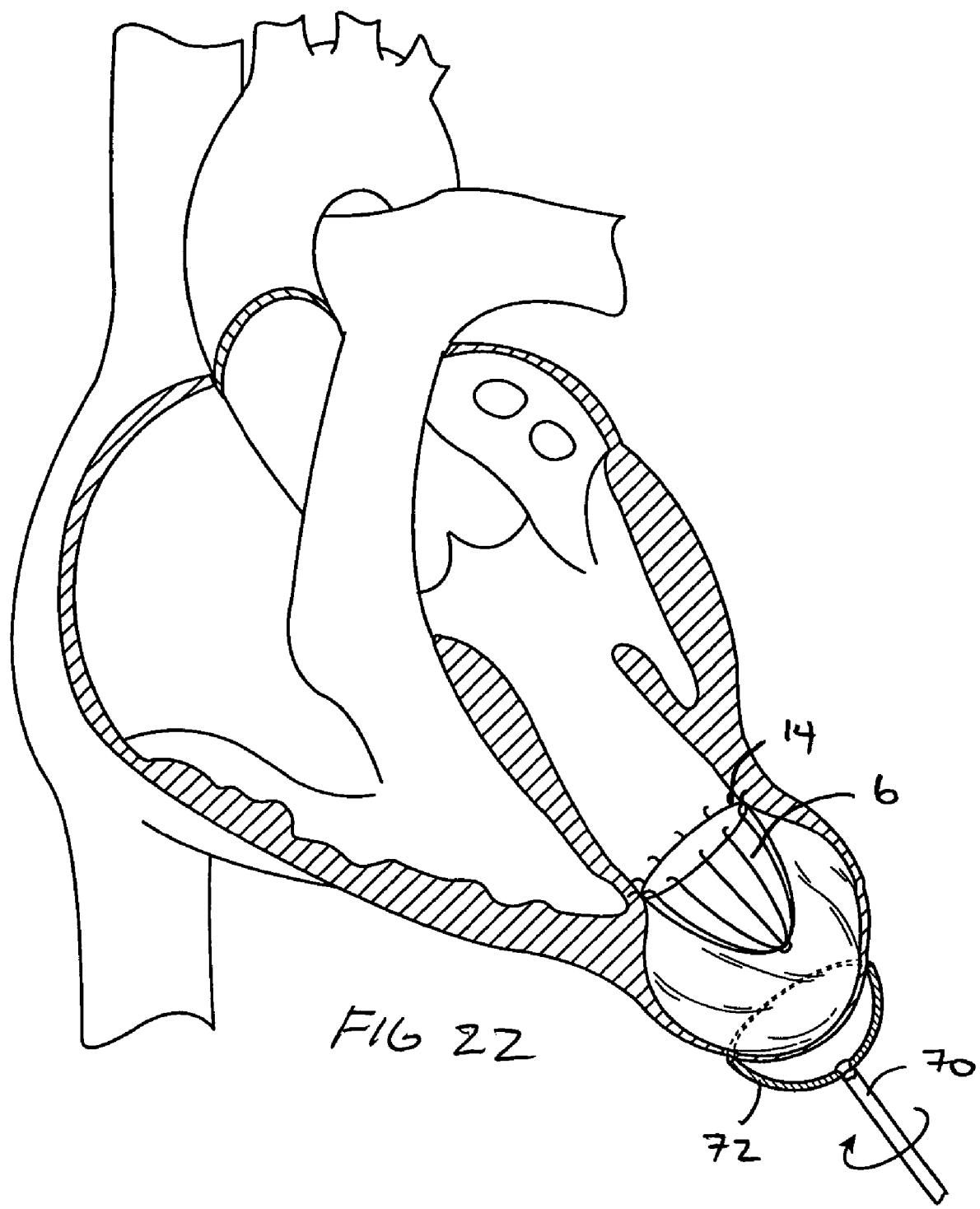
FIG. 22 shows another tool used to twist the heart.
Figure 23:
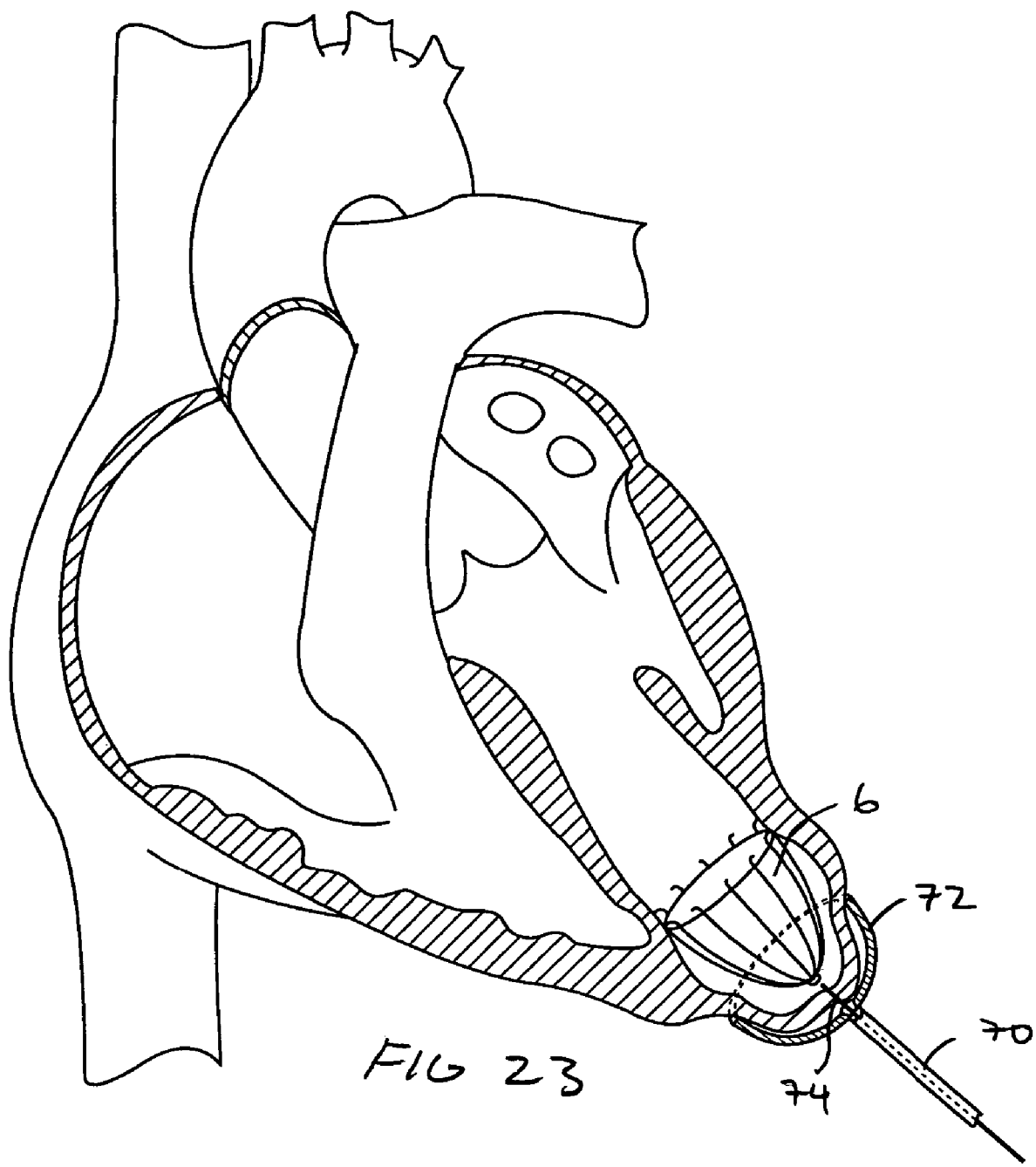
FIG. 23 shows the heart twisted and the non-blood flow side evacuated using the tool.
Figure 24:
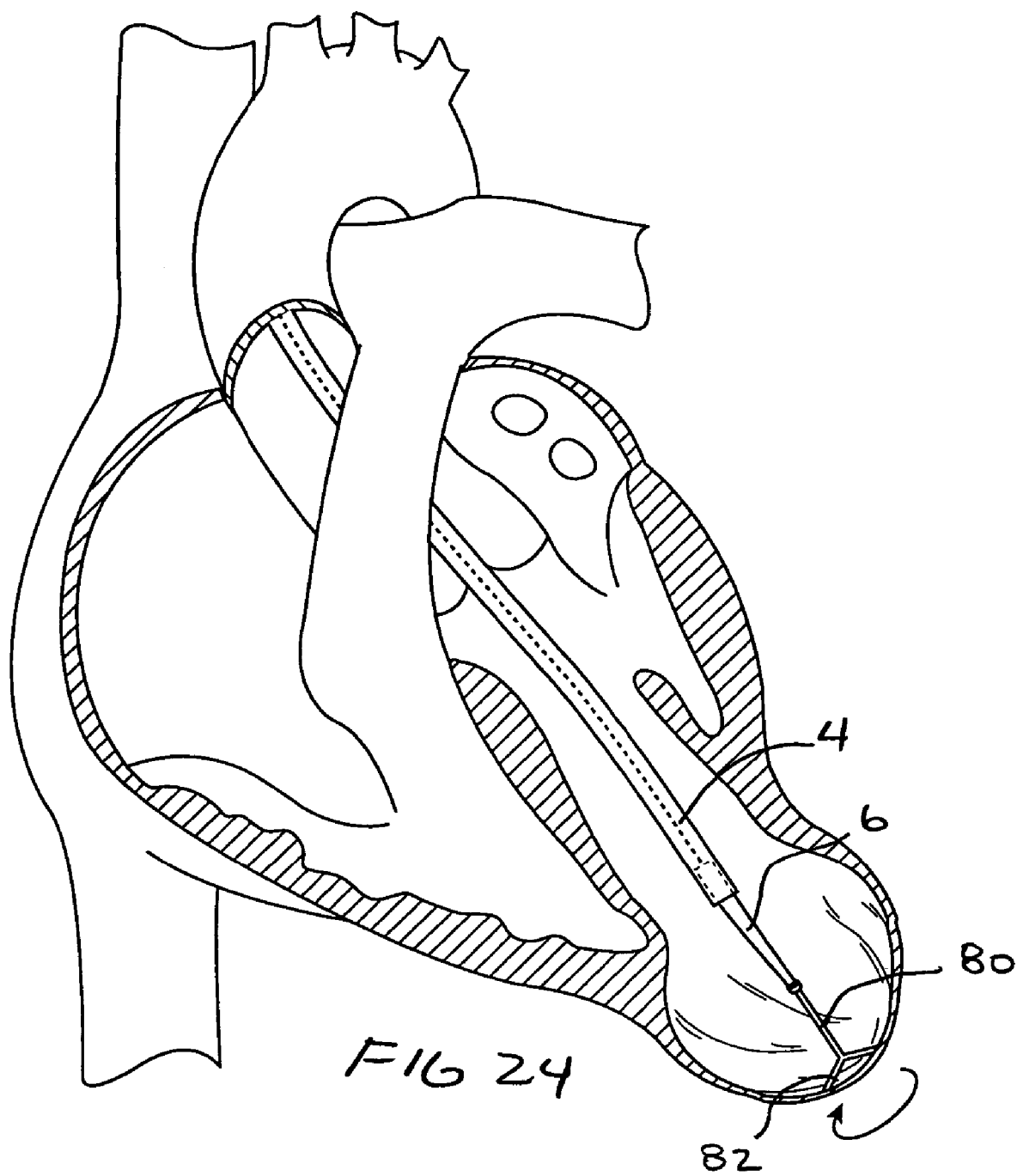
FIG. 24 shows an endovascular tool for twisting the heart.
Figure 25:
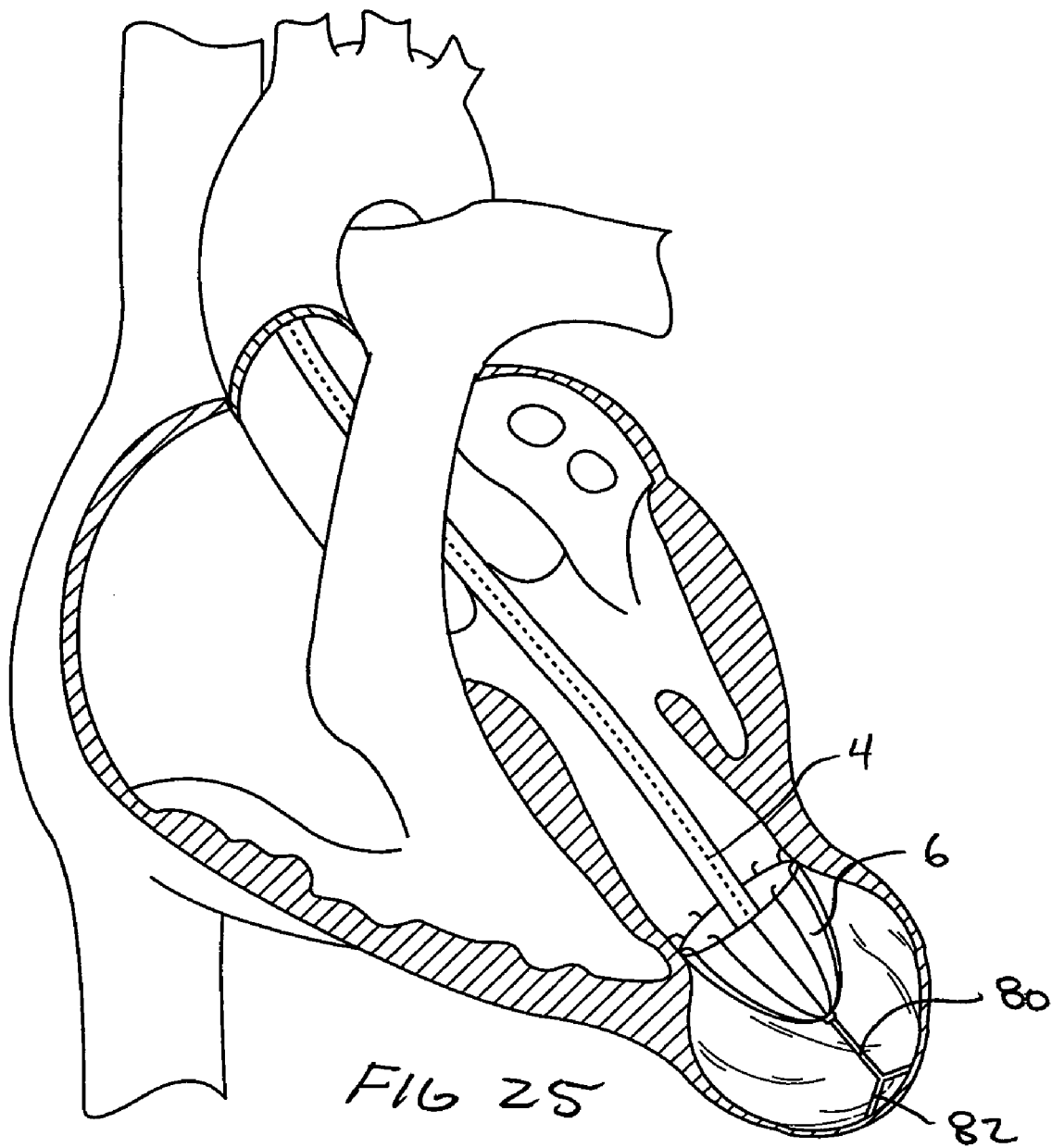
FIG. 25 shows the element expanded while the heart is twisted.
Figure 26:
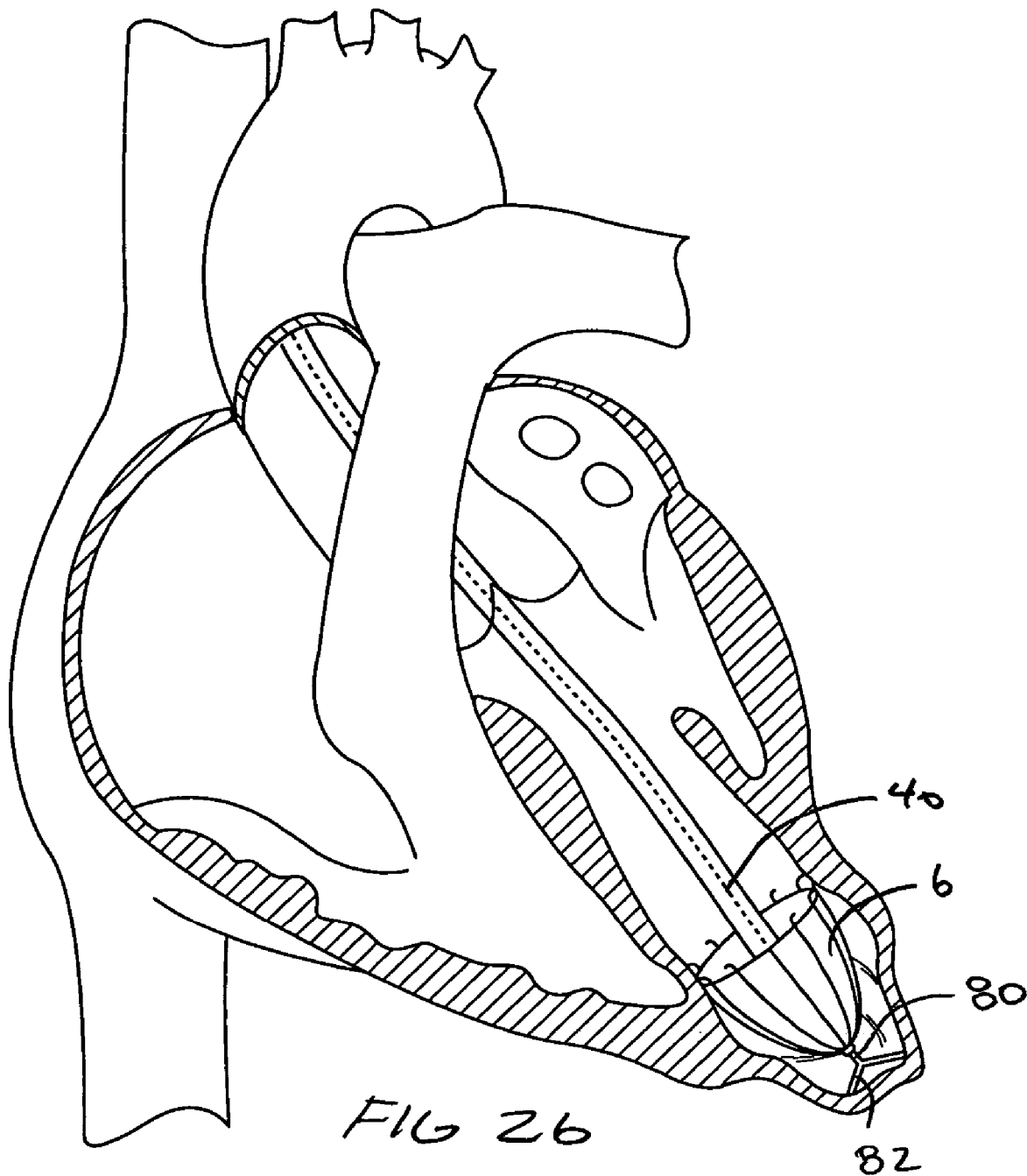
FIG. 26 shows the non-blood flow side collapsed.
Figure 27:
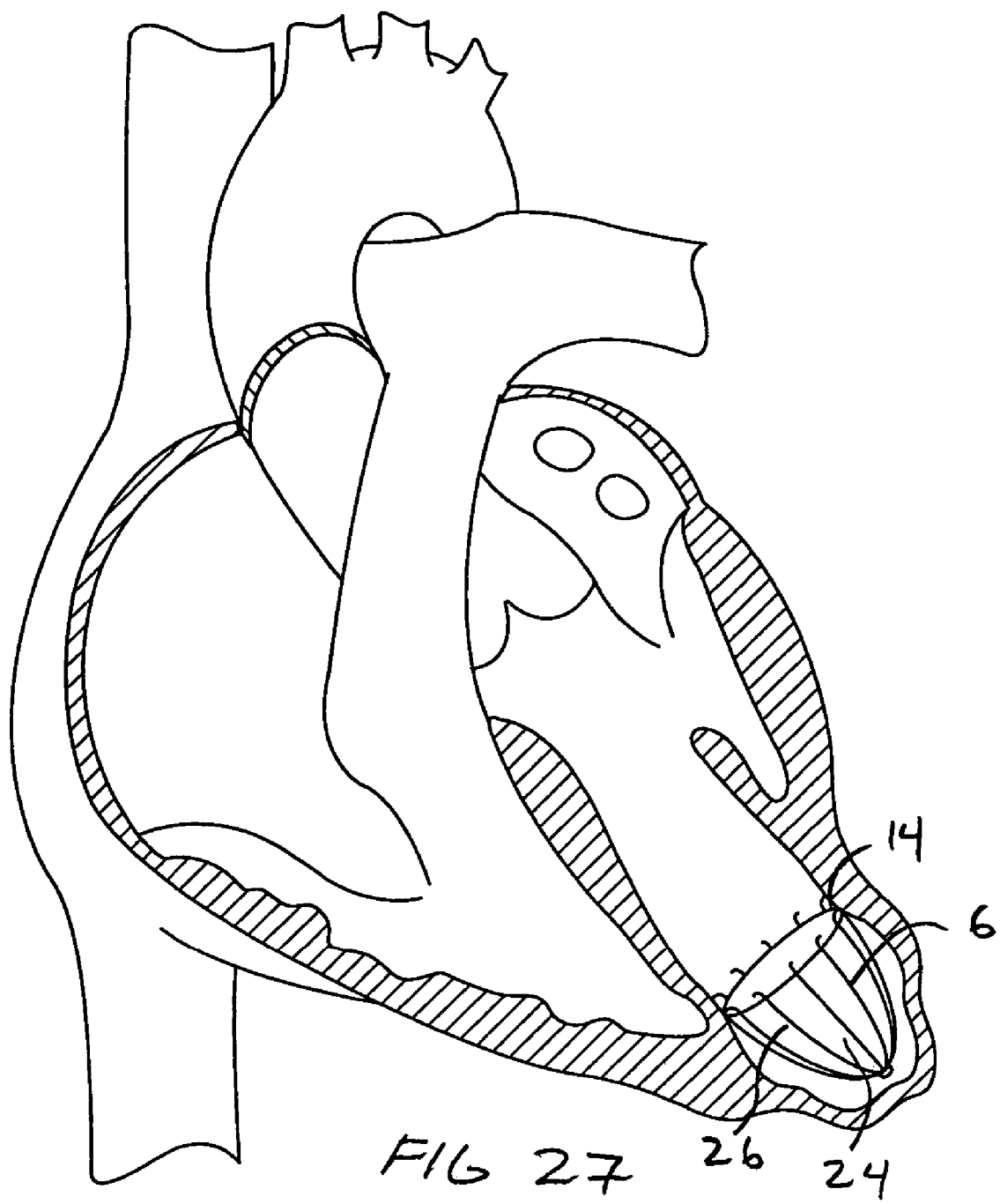
FIG. 27 shows the non-blood flow side collapsed and attached to the element in a biased position.

It may also be desirable to twist the heart, such as in the direction favoring contraction of the left ventricle, so that the element 6 and/or left ventricle is naturally biased toward the contracted state. Referring to FIGS. 22 and 23, for example, the heart may be twisted and then anchored to the element 6 to maintain a torsional load on the heart. A heart twisting tool 70 may include a suction cup 72 or other device for holding and engaging the heart. The tool 70 may also have a needle 74 or the like to pierce and evacuate the non-blood flow side as mentioned above. The tool 70 is used to twist or rotate the heart and then evacuate the blood as shown in FIG. 23. The tool 70 may be used prior to expanding the element 6 so that the element 6 itself helps the heart wall to retain the desired shape. Referring to FIGS. 25-27, the delivery device 4 itself may also have an element 80 which engages and twists the heart. The element 80 may simply be a relatively robust wire or tube having piercing elements 82 which pierce the heart wall and transmit torque to the heart. The isolated or non-blood flow side may then be evacuated and the element 6 withdrawn to permit the heart to collapse and remodel as described herein and shown in FIGS. 26 and 27. Thus, it can be appreciated that the heart may be displaced or distorted before attaching the element 6 to the left ventricle. Of course, the heart may be twisted or torqued before, during or after evacuating blood from the isolated region to provide the desired loads, displacement and/or shape of the heart.

The wall of the left ventricle may also be attached to the element 6 apart from the circumferential connection to the element 6. In this manner, the desired changes in the shape of the heart, which may be thought of as partial or complete remodeling of the heart, is maintained. Referring again to FIG. 19, the tool 63 may be used to secure the left ventricle to the element 6. The element 6 may be attached to the heart using the attachment element 65 driven through the heart and into engagement with the element 6. The attachment element 65 may be the suture 67 or any suitable structure such as a staple, suture, or anchor. Of course, the attachment element 65 may also be driven into the wall of the left ventricle from within the left ventricle using the delivery device 4 or another suitable device. The attachment element 65 is driven through the wall of the left ventricle after expansion of the element 6 and may occur after manipulating the heart as desired. The wall of the left ventricle may also be attached to the element 6 using an energy source, such as RF, which attaches or adheres the element 6 to the wall of the left ventricle similar to the tool 62 of FIG. 18.

Figure 28:
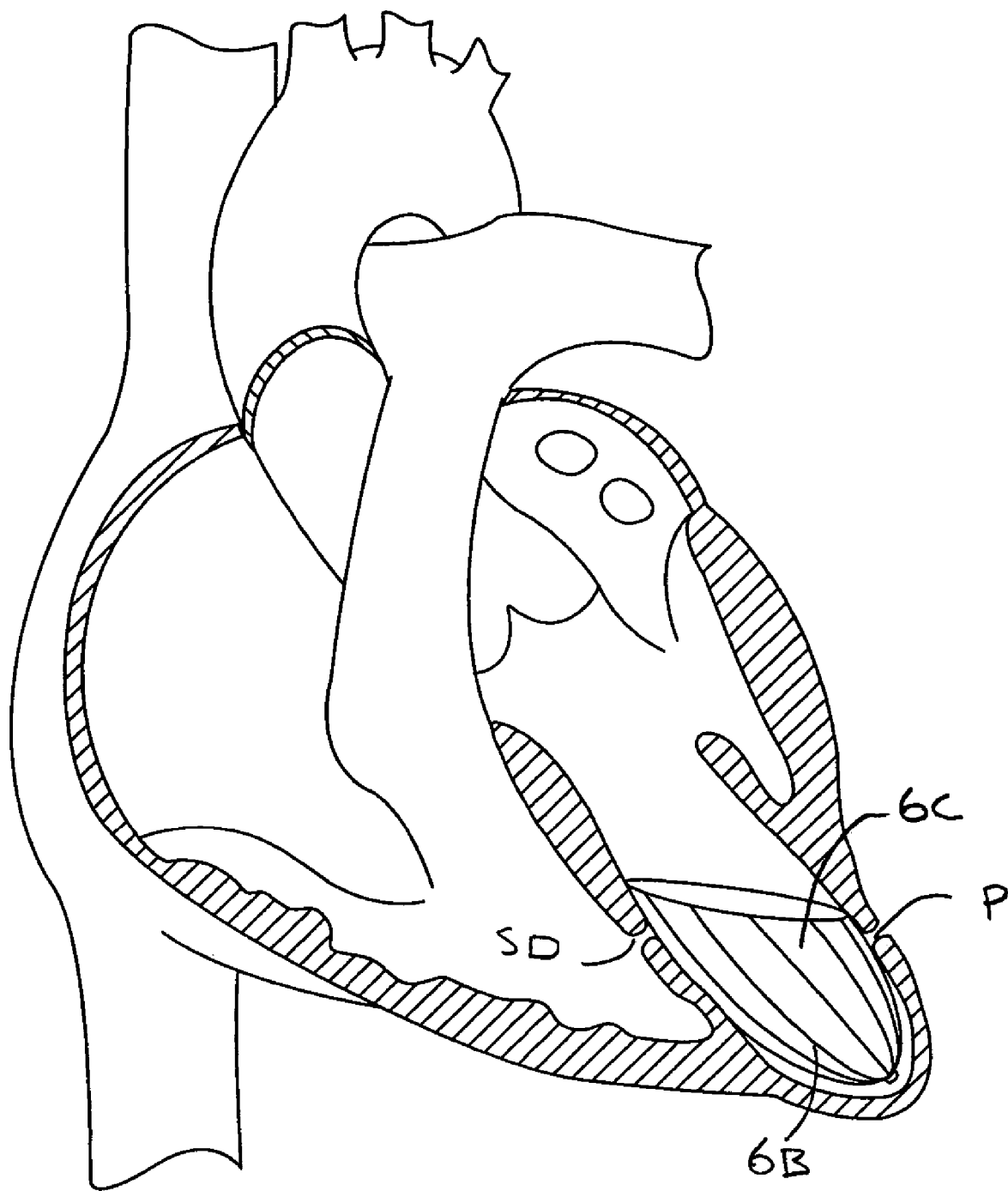
FIG. 28 shows the element extending obliquely along the septum to exclude a ventricular septal defect, free ventricular wall perforation or exclusion of akinetic ventricular septum or wall.

The present invention also provides the ability to treat a septal defect SD or other opening or tear in the septum or a perforation P in the left ventricle free wall by isolating the defect or opening by isolating that portion with the element as shown in FIG. 28. The element 6C may be delivered endovascularly or percutaneously providing obvious advantages over a purely surgical procedure. The element 6C of FIG. 28 may have a more elliptical opening depending upon the desired geometry of the element 6C and the heart. The element 6C may also be used to treat a perforation of the left ventricle as also shown in FIG. 28.

The element 6 may also be delivered directly through a penetration in the left ventricle. Referring to FIGS. 8-11, for example, the left ventricle may be accessed directly through a surgical incision in the left ventricle. The delivery device 4 is introduced through the opening in the left ventricle with purse string sutures 81 maintaining hemostasis. This procedure, and deployment of the element 6, may take place under bypass or while the heart is beating. If the patient's heart has non-functioning regions near the apex, such as is often the case with a dilated or ischemic heart, working through an opening in that part of the heart, such as near the apex, may be easier to maintain while the heart is beating. After introduction through the opening in the left ventricle wall or endovascular delivery as described herein, the element 6 is expanded in the left ventricle in any suitable manner. The element 6 may be expanded by itself or expanded with the balloon 12 (FIG. 3) or a mechanical device. Furthermore, any suitable tool, such as those described herein, may be used to manipulate the heart or to secure the element 6 to the left ventricle wall as described above and those methods and devices are expressly incorporated here.

Depending upon the particular cardiac condition being treated, the element 6 may also help reduce future dilation of an already dilated heart. First, the isolated area is often a non-functioning and/or dilated region. Eliminating or reducing blood flow pressure in the isolated area may reduce or prevent further dilation due to the blood pressure. The element 6 also provides a mechanical advantage to the dilated left ventricle by isolating the non-contracting and dilated segments. The element 6 may also reduce the radius of curvature of the non-isolated and/or functioning portion of the left ventricular wall. The reduction in radius of curvature may reduce wall stress and work of the non-isolated area. Finally, the element 6 may also provide physical support for the heart to reduce or prevent further dilation and also provide physical remodeling of the heart and a mechanical advantage which can further reduce dilation.

It can be appreciated that the present invention may be practiced in a number of different ways with varying devices without departing from the scope of the invention. For example, the element may be attached closer to the apex or the element may be formed from two or more parts delivered independently.

What is claimed is:

1. A method of altering blood flow through the left ventricle, comprising the steps of:
   providing an element which is movable between collapsed and expanded conditions;
   collapsing the element in a delivery device;
   advancing the element into the left ventricle in the collapsed condition with the delivery device;
   expanding the element in the left ventricle;
   evacuating blood from a non-blood flow side after the expanding step; and
   securing the element to the wall of the left ventricle to form a circumferential attachment to the wall of the left ventricle, wherein the element separates the left ventricle into a blood flow side and the non-blood flow side, the element forming a hemostatic seal at the circumferential attachment so that pressure in the blood flow side is not communicated to the non-blood flow side thereby reducing pressure on the ventricular wall of the non-blood flow side.

2. The method of claim 1, wherein:
   the securing step is carried out with the circumferential attachment being below the papillary muscles.

3. The method of claim 2, wherein:
   the securing step is carried out with the circumferential attachment being within 1 cm of the papillary muscles.

4. The method of claim 1, wherein:
   the advancing step is carried out with the element being delivered through a peripheral vessel, through the aortic valve and into the left ventricle.

5. The method of claim 1, wherein:
   the advancing step is carried out with the element being delivered through a wall of the left ventricle.

6. The method of claim 1, wherein:
   the securing step is carried out with the circumferential attachment separating the left ventricle into a blood flow side and a non-blood flow side, the blood flow side being a side in which blood circulates through the heart.

7. The method of claim 1, wherein:
   the expanding step is carried out with the element having an outer surface which is at least partly separated from the inner wall of the left ventricle to form the non blood flow side.

8. The method of claim 7, wherein:
the providing step is carried out with the outer surface of the element being generally shaped to provide a desired geometry of the left ventricle wall.

9. The method of claim 7, wherein:
the providing step is carried out with the outer surface of the element being generally convex and having an apex when in the expanded position.

10. The method of claim 1, wherein: the securing step is carried out without cutting a wall of the left ventricle.

11. The method of claim 1, wherein:
the evacuating step is carried out until at least part of the left ventricle wall moves into contact with the element.

12. The method of claim 1, further comprising the step of:
introducing a tool into the chest;
engaging the heart with the tool; and
securing the element in the left ventricle using the tool.

13. The method of claim 12, wherein:
the securing step is carried out with the tool extending through a portion of the left ventricle which is part of an isolated portion of the left ventricle, the isolated portion not forming part of a blood flow path through the left ventricle.

14. The method of claim 12, wherein:
the securing step is carried out by driving an anchor through the wall of the left ventricle and into engagement with the element.

15. The method of claim 12, wherein:
the securing step is carried out with the tool having an energy source, the energy source being activated to secure the element to the wall of the left ventricle.

16. The method of claim 12, wherein:
the securing step is carried out by displacing the heart before securing the element to the left ventricle using the tool.

17. The method of claim 1, further comprising the step of:
everting the element within the left ventricle.

18. The method of claim 17, further comprising the step of:
evacuating blood from an isolated region of the left ventricle;
the expanding step being carried out with the element contacting the wall thereby separating the left ventricle into a blood flow side and the isolated side;
the everting step being carried out after the evacuating step.

19. The method of claim 1, wherein:
the providing step is carried out with the delivery device having a filter, the filter being movable between collapsed and expanded positions.

20. The method of claim 19, further comprising the step of:
expanding the filter to the expanded position before at least one of the expanding and securing steps.

21. The method of claim 19, further comprising the step of:
expanding the filter in the left ventricle.

22. The method of claim 1, further comprising the step of:
displacing the heart to a displaced condition; and
holding the heart in the displaced condition using the element.

23. The method of claim 22, wherein:
the displacing step is carried out by twisting the heart.

24. The method of claim 22, wherein:
the displacing step is carried out with a tool extending into the chest through an opening in the chest, the tool engaging an external surface of the heart.

25. The method of claim 22, further comprising the step of:
attaching the heart to the element using an anchoring device extending between the heart and the element.

26. The method of claim 22, wherein:
the displacing step is carried out with the heart being displaced by the element.

27. The method of claim 1, wherein:
the providing step is carried out with a size of the element being selected before the delivering step.

28. The method of claim 1, wherein:
the providing step is carried out with the element being sized to extend across a predetermined part of the left ventricle below the papillary muscles.

29. The method of claim 1, wherein:
the providing step is carried out with the element including a convex outer surface having an apex.

30. The method of claim 1, wherein:
the providing step is carried out with the element having a plurality of support members extending toward the apex.

31. The method of claim 1, further comprising the step of:
collapsing the element after the expanding step;
repositioning the element after the collapsing step; and
reexpanding the element after the repositioning step.

32. A method of altering blood flow through the left ventricle, comprising the steps of:
providing an element which is movable from a collapsed position to an expanded position;
advancing the element into a left ventricle using a delivery device, the element being in the collapsed position while in the delivery device;
expanding the element within the left ventricle;
securing the element to an inner wall of the left ventricle at a position below the papillary muscles so that the element separates the left ventricle into a blood flow side and an isolated side, wherein the blood flow side forms part of a blood flow path through the heart and the isolated side does not; and
evacuating blood from the isolated side after the expanding step.

33. The method of claim 32, wherein:
the securing step is carried out with the circumferential attachment being below the papillary muscles.

34. The method of claim 33, wherein:
the securing step is carried out with the circumferential attachment being within 1 cm of the papillary muscles.

35. The method of claim 32, wherein:
the advancing step is carried out with the element being delivered through a peripheral vessel, through the aortic valve and into the left ventricle.

36. The method of claim 33, wherein:
the advancing step is carried out with the element being delivered through a wall of the left ventricle.

37. The method of claim 32, wherein:
the securing step is carried out with the circumferential attachment separating the left ventricle into a blood flow side and a non-blood flow side, the blood flow side being a side in which blood circulates through the heart.

38. The method of claim 32, wherein:
the expanding step is carried out with the element having an outer surface which is at least partly separated from the inner wall of the left ventricle to form an isolated portion of the left ventricle.

39. The method of claim 38, wherein:
the providing step is carried out with the outer surface of the element being generally shaped to provide a desired geometry of the left ventricle wall.

40. The method of claim 38, wherein:
the providing step is carried out with the outer surface of the element being generally convex and having an apex when in the expanded position.

41. The method of claim 32, wherein:
the securing step is carried out without cutting a wall of the left ventricle.

42. The method of claim 32, wherein:
the evacuating step is carried out until at least part of the left ventricle wall moves into contact with the element.

43. The method of claim 32, further comprising the step of:
introducing a tool into the chest; and
engaging the heart with the tool;
wherein the securing step is carried out with the element being secured in the left ventricle using the tool.

44. The method of claim 43, wherein:
the securing step is carried out with the tool extending through a portion of the left ventricle which is part of an isolated portion of the left ventricle, the isolated portion not forming part of a blood flow path through the left ventricle.

45. The method of claim 43, wherein:
the securing step is carried out by driving an anchor through the wall of the left ventricle and into engagement with the element.

46. The method of claim 43, wherein:
the securing step is carried out with the tool having an energy source, the energy source being activated to secure the element to the wall of the left ventricle.

47. The method of claim 43, wherein:
the securing step is carried out by displacing the heart before securing the element to the left ventricle using the tool.

48. The method of claim 32, further comprising the step of:
everting the element within the left ventricle.

49. The method of claim 48, further comprising the step of:
evacuating blood from an isolated region of the left ventricle;
the expanding step being carried out with the element contacting the wall thereby separating the left ventricle into a blood flow side and the isolated side;
the everting step being carried out after the evacuating step.

50. The method of claim 32, wherein:
the providing step is carried out with the delivery device having a filter, the filter being movable between collapsed and expanded positions.

51. The method of claim 50, further comprising the step of:
expanding the filter to the expanded position before at least one of the expanding and securing steps.

52. The method of claim 50, further comprising the step of:
expanding the filter in the left ventricle.

53. The method of claim 32, further comprising the step of:
displacing the heart to a displaced condition; and
holding the heart in the displaced condition using the element.

54. The method of claim 53, wherein:
the displacing step is carried out by twisting the heart.

55. The method of claim 53, wherein:
the displacing step is carried out with a tool extending into the chest through an opening in the chest, the tool engaging an external surface of the heart.

56. The method of claim 53, further comprising the step of:
attaching the heart to the element using an anchoring device extending between the heart and the element.

57. The method of claim 53, wherein:
the displacing step is carried out with the heart being displaced by the element.

58. The method of claim 32, wherein:
the providing step is carried out with a size of the element being selected before the delivering step.

59. The method of claim 32, wherein:
the providing step is carried out with the element being sized to extend across a predetermined part of the left ventricle below the papillary muscles.

60. The method of claim 32, wherein:
the providing step is carried out with the element including a convex outer surface having an apex.

61. The method of claim 32, wherein:
the providing step is carried out with the element having a plurality of support members extending toward the apex.

62. The method of claim 32, further comprising the step of:
collapsing the element after the expanding step;
repositioning the element after the collapsing step; and
reexpanding the element after the repositioning step.

63. A method of altering blood flow through the left ventricle, comprising the steps of:
providing an element which is movable between collapsed and expanded conditions;
collapsing the element in a delivery device;
advancing the element into the left ventricle in the collapsed condition with the delivery device;
expanding the element in the left ventricle;
securing the element to the wall of the left ventricle to separate the left ventricle into a blood flow side and a non-blood flow side; and
reducing the volume of the non-blood flow side after the expanding step until at least part of the left ventricle wall moves into contact with the element.

64. The method of claim 63, further comprising the step of:
maintaining a reduced volume in the non-blood flow side.

65. The method of claim 63, wherein:
the reducing step is carried out by evacuating blood from the non-blood flow side.

66. The method of claim 63, wherein:
the reducing step is carried out by manipulating the wall of the left ventricle on the non-blood flow side to reduce the volume of the non-blood flow side.

67. The method of claim 63, wherein:
the reducing step is carried out with the element forming a seal which prevents blood from passing from the blood flow side to the non-blood flow side.

68. The method of claim 63, wherein:
the reducing step is carried out with the element forming a hemostatic seal with the wall of the left ventricle.

69. The method of claim 63, wherein:
the securing step is carried out with the element forming a hemostatic seal at the circumferential attachment so that pressure in the blood flow side is not communicated to the non-blood flow side thereby reducing pressure on the ventricular wall of the non-blood flow side.

70. The method of claim 63, wherein:
the securing step is carried out with the circumferential attachment being below the papillary muscles.

71. The method of claim 70, wherein:
the securing step is carried out with the circumferential attachment being within 1 cm of the papillary muscles.

72. The method of claim 63, wherein:
the advancing step is carried out with the element being delivered through a wall of the left ventricle.

73. The method of claim 63, wherein:
the providing step is carried out with an outer surface of the element being generally shaped to provide a desired geometry of the left ventricle wall.

74. The method of claim 73, wherein:
the providing step is carried out with the outer surface of the element being generally convex and having an apex when in the expanded position.

75. The method of claim 63, further comprising the step of:
introducing a tool into the chest;
engaging the heart with the tool; and
securing the element in the left ventricle using the tool.

76. The method of claim 63, wherein:
the securing step is carried out with the tool extending through a portion of the left ventricle which is part of an isolated portion of the left ventricle, the isolated portion not forming part of a blood flow path through the left ventricle.

77. The method of claim 63, wherein:
the securing step is carried out by driving an anchor through the wall of the left ventricle and into engagement with the element.

78. The method of claim 63, wherein:
the securing step is carried out using a tool having an energy source, the energy source being activated to secure the element to the wall of the left ventricle.

79. The method of claim 63, wherein:.
the securing step is carried out by displacing the heart before securing the element to the left ventricle using the tool.

80. The method of claim 63, further comprising the step of:
everting the element within the left ventricle.

81. The method of claim 63, further comprising the step of:
evacuating blood from an isolated region of the left ventricle;
the expanding step being carried out with the element contacting the wall thereby separating the left ventricle into a blood flow side and the isolated side;
the everting step being carried out after the evacuating step.

82. The method of claim 63, wherein:
the providing step is carried out with the delivery device having a filter, the filter being movable between collapsed and expanded positions.

83. The method of claim 82, further comprising the step of:
expanding the filter to the expanded position before at least one of the expanding and securing steps.

84. The method of claim 82, further comprising the step of:
expanding the filter in the left ventricle.

85. The method of claim 63, further comprising the step of:
displacing the heart to a displaced condition; and
holding the heart in the displaced condition using the element.

86. The method of claim 85, wherein:
the displacing step is carried out by twisting the heart.

87. The method of claim 85, wherein:
the displacing step is carried out with a tool extending into the chest through an opening in the chest, the tool engaging an external surface of the heart.

88. The method of claim 63, wherein:
the providing step is carried out with a size of the element being selected before the delivering step.

89. The method of claim 63, further comprising the step of:
collapsing the element after the expanding step;
repositioning the element after the collapsing step; and
reexpanding the element after the repositioning step.

* * * * *